US006350731B1

(12) United States Patent
Jehanli et al.

(10) Patent No.: US 6,350,731 B1
(45) Date of Patent: Feb. 26, 2002

(54) PLATELET-DERIVED GROWTH FACTOR ANALOGUES

(75) Inventors: Ahmed Mohammed Taki Jehanli, Mitcham; Geeta Patel; Yemisi Olabiran, both of London; David Mark Brennand, Staple Grove; Vir Vijay Kakkar, Bickley, all of (GB)

(73) Assignee: Trigen Limited, London (GB)

( * ) Notice: Subject to any disclaimer, the term of this patent is extended or adjusted under 35 U.S.C. 154(b) by 0 days.

(21) Appl. No.: 09/432,879

(22) Filed: Nov. 2, 1999

Related U.S. Application Data

(62) Division of application No. 08/635,007, filed on Apr. 19, 1996, now Pat. No. 5,952,304.

(30) Foreign Application Priority Data

| | | |
|---|---|---|
| Oct. 22, 1993 | (GB) | 9321861 |
| Jan. 4, 1994 | (GB) | 9400022 |

(51) Int. Cl.[7] .......................... A61K 38/04; C07K 7/00

(52) U.S. Cl. .............................. 514/12; 514/2; 514/13; 514/14; 514/15; 530/327; 530/328; 530/399; 424/185.1

(58) Field of Search ................................ 514/2, 12–15; 530/327, 328, 399; 424/185.1

(56) References Cited

U.S. PATENT DOCUMENTS

| | | | | |
|---|---|---|---|---|
| 5,183,805 A | * | 2/1993 | Lee et al. | 514/13 |
| 5,326,695 A | | 7/1994 | Andersson et al. | 435/70.1 |
| 5,591,587 A | | 1/1997 | Niman | 435/7.1 |
| 5,700,444 A | * | 12/1997 | Zamora et al. | 424/1.69 |

FOREIGN PATENT DOCUMENTS

| | | | |
|---|---|---|---|
| WO | 93/16719 | | 9/1993 |
| WO | 93/23068 | * | 11/1993 |
| WO | 93/25576 | | 12/1993 |

OTHER PUBLICATIONS

Engstrom et al. J. Biol. Chem. vol. 267, No. 23 pp. 16581–16587, Aug. 1992.*

* cited by examiner

*Primary Examiner*—Bennett Celsa
(74) *Attorney, Agent, or Firm*—Richard F. Trecartin; Todd A. Lorenz; Flehr Hohbach Test Albritton & Herbert LLC

(57) ABSTRACT

Novel peptide analogues of platelet-derived growth factor, for use in inhibiting or stimulating growth and/or chemotaxis of cells, for example, smooth muscle cells, are provided. Also provided are compositions of matter comprising those peptide analogues.

13 Claims, 16 Drawing Sheets

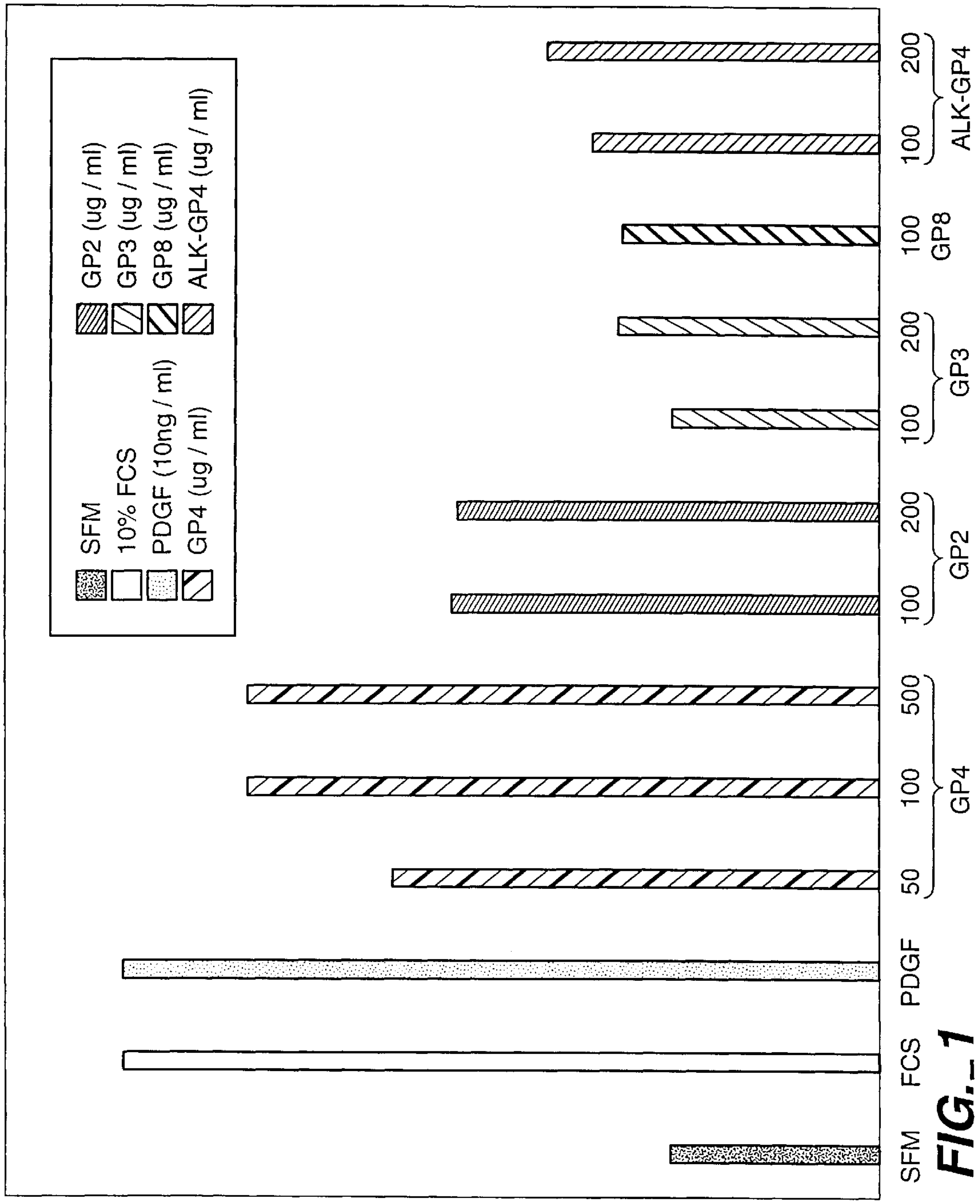
FIG._1

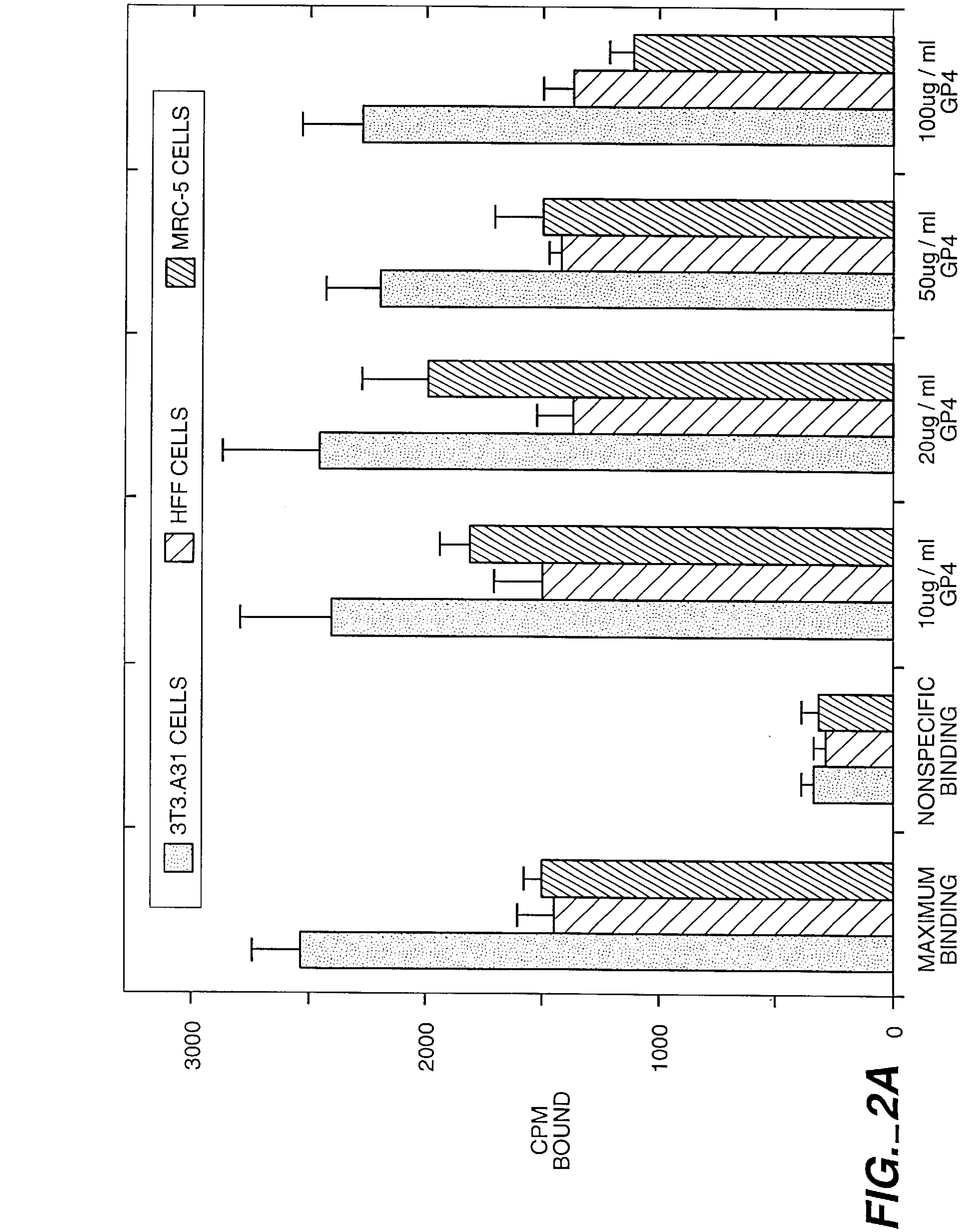
FIG._2A

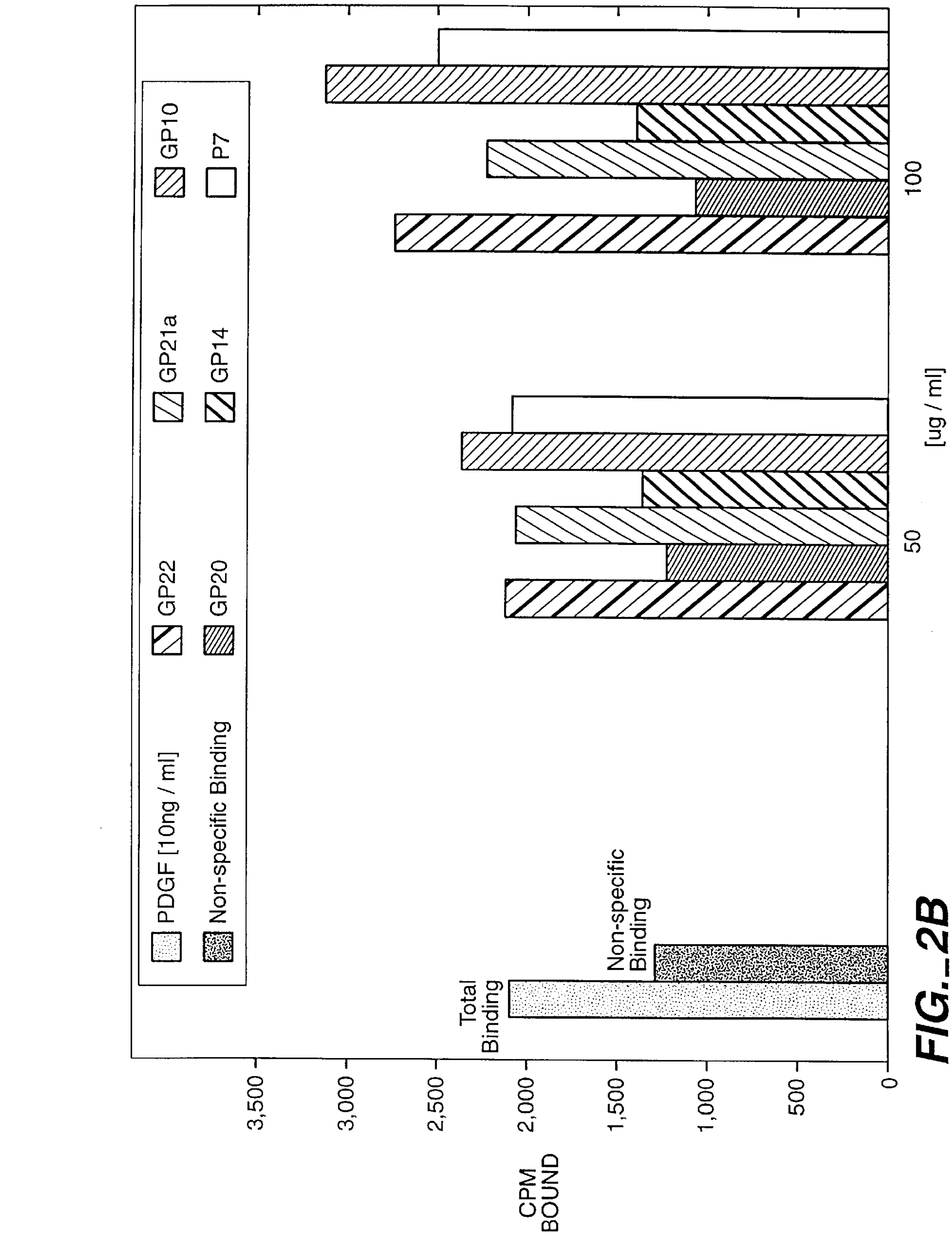
FIG._2B

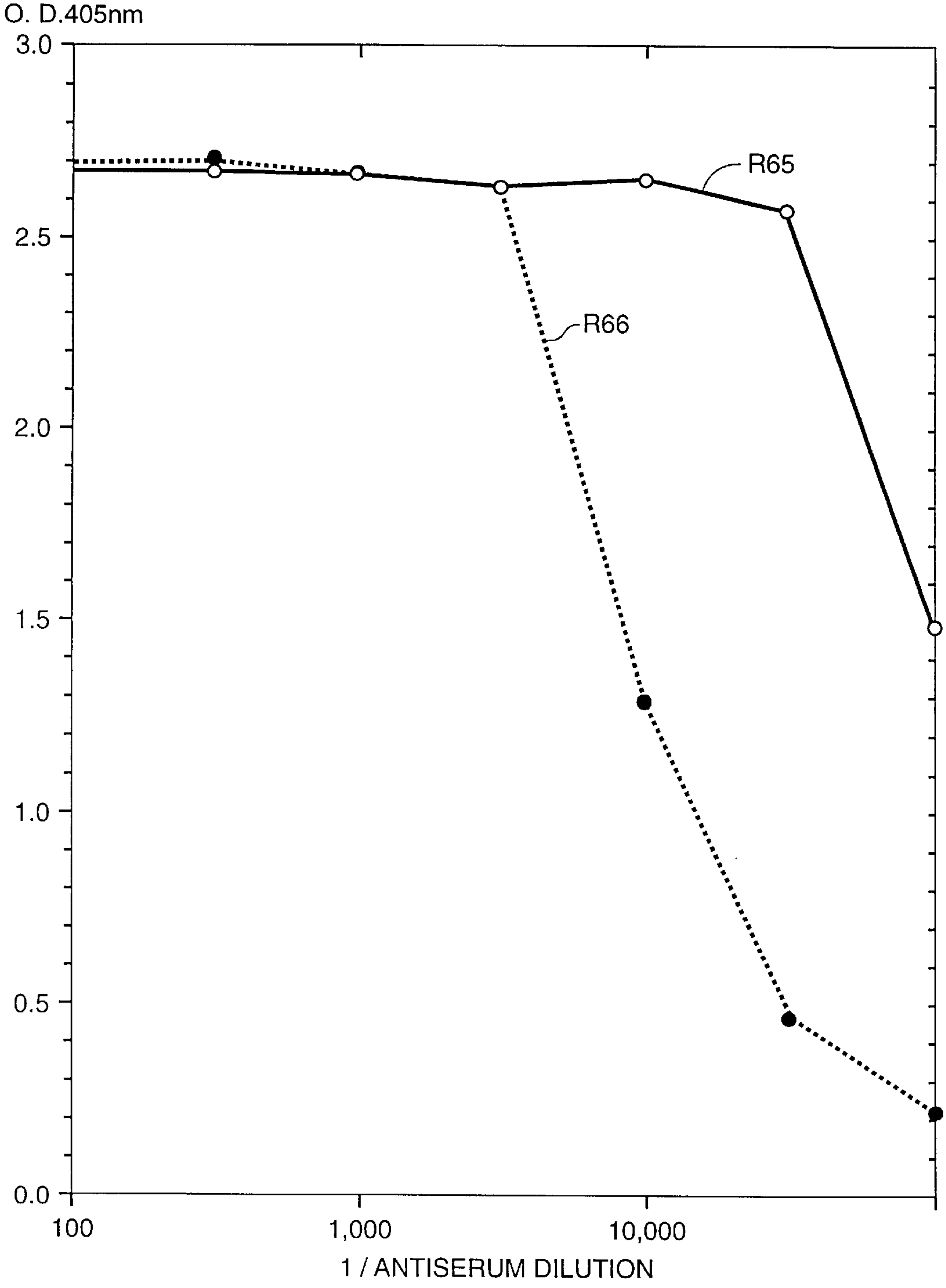
FIG._3A

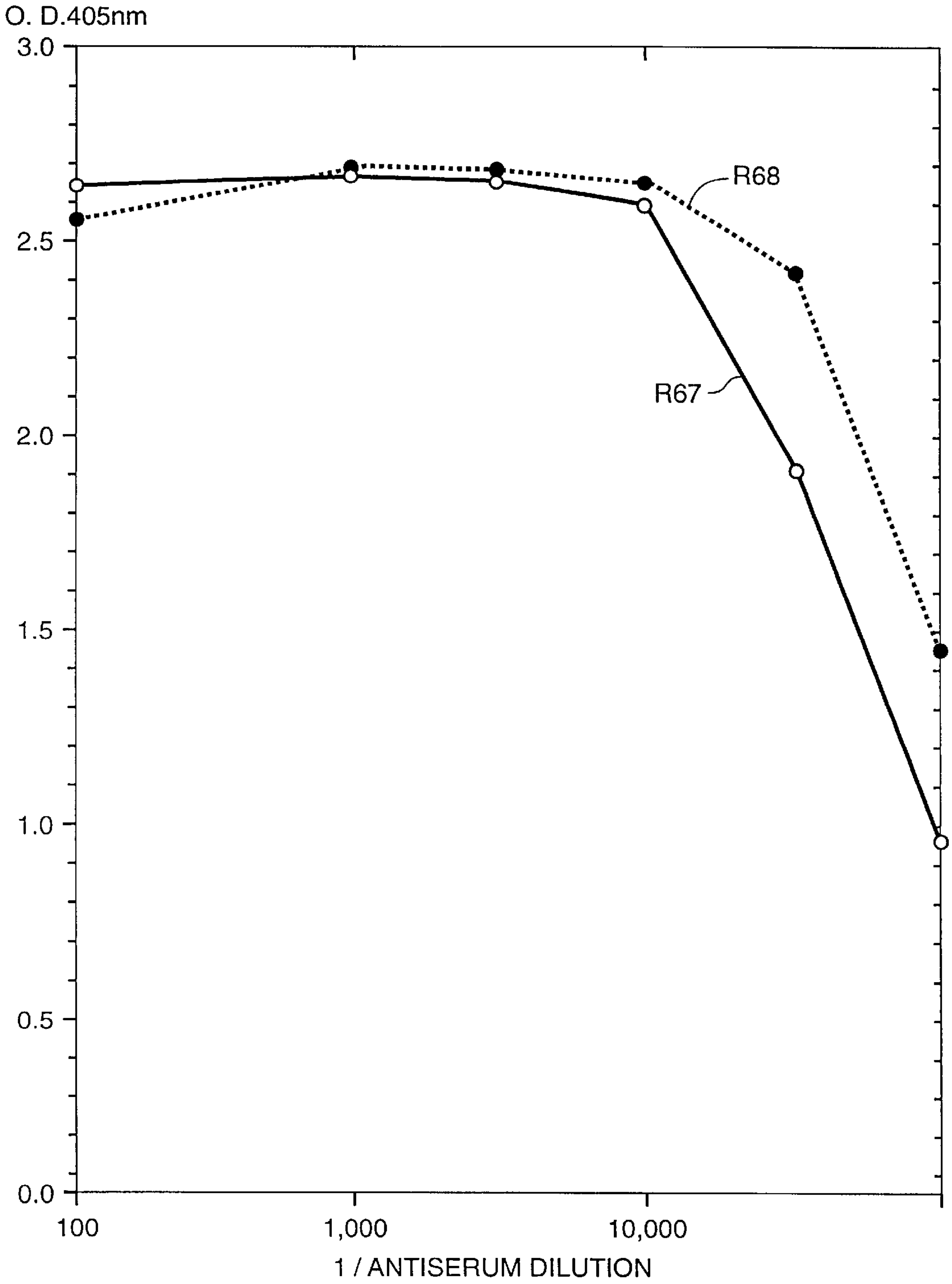
FIG._3B

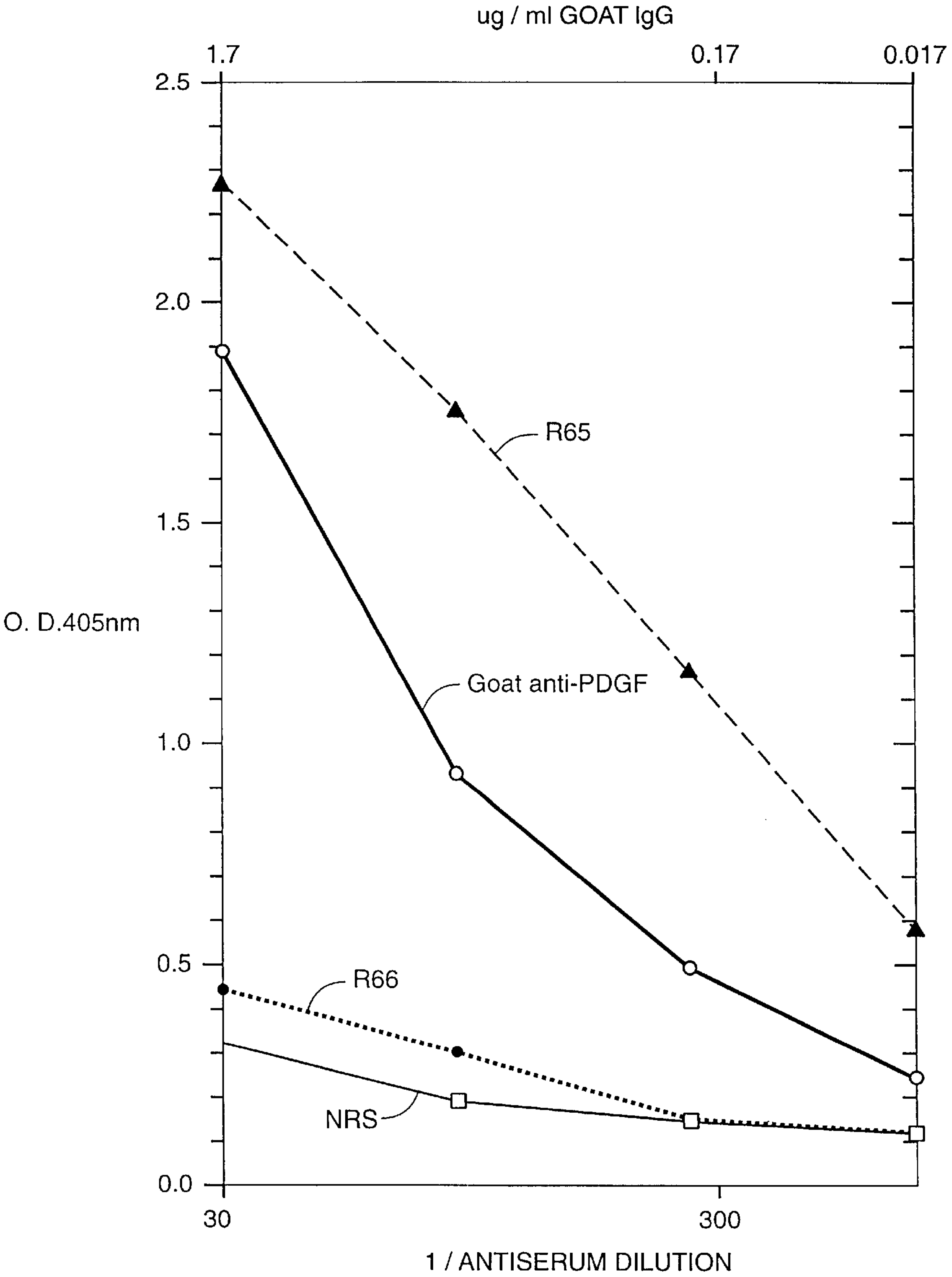
FIG._4A

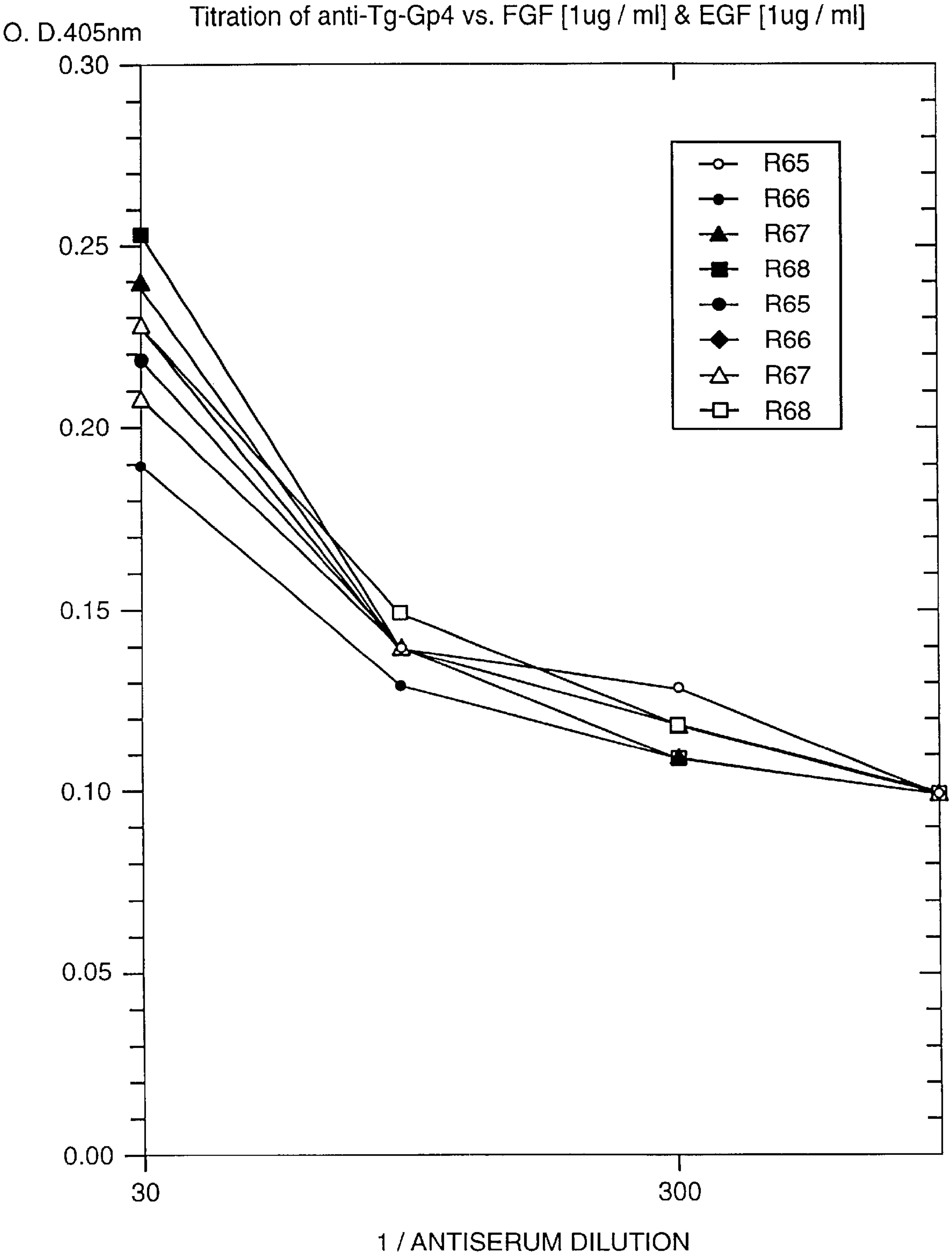
FIG._4B

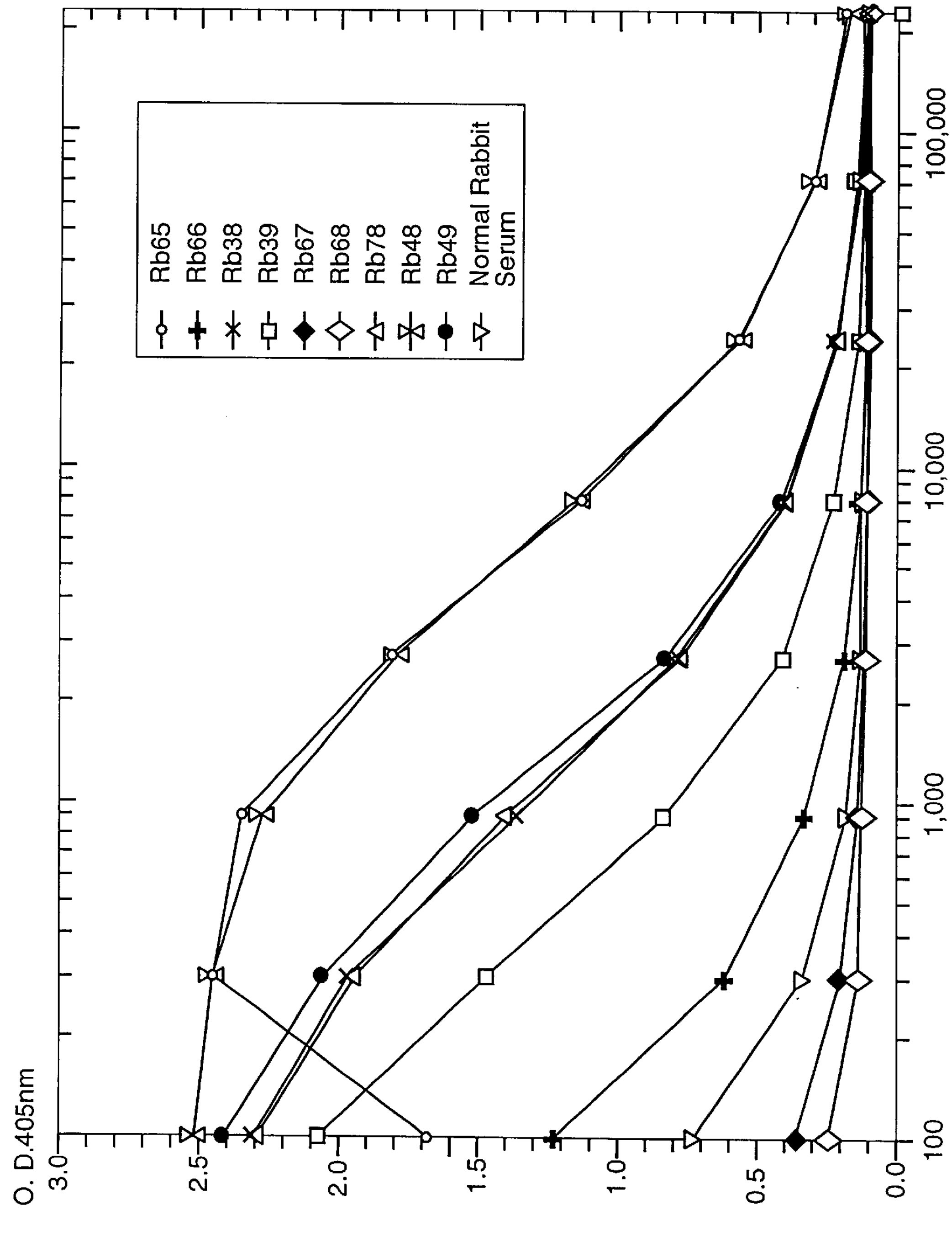
FIG._5A

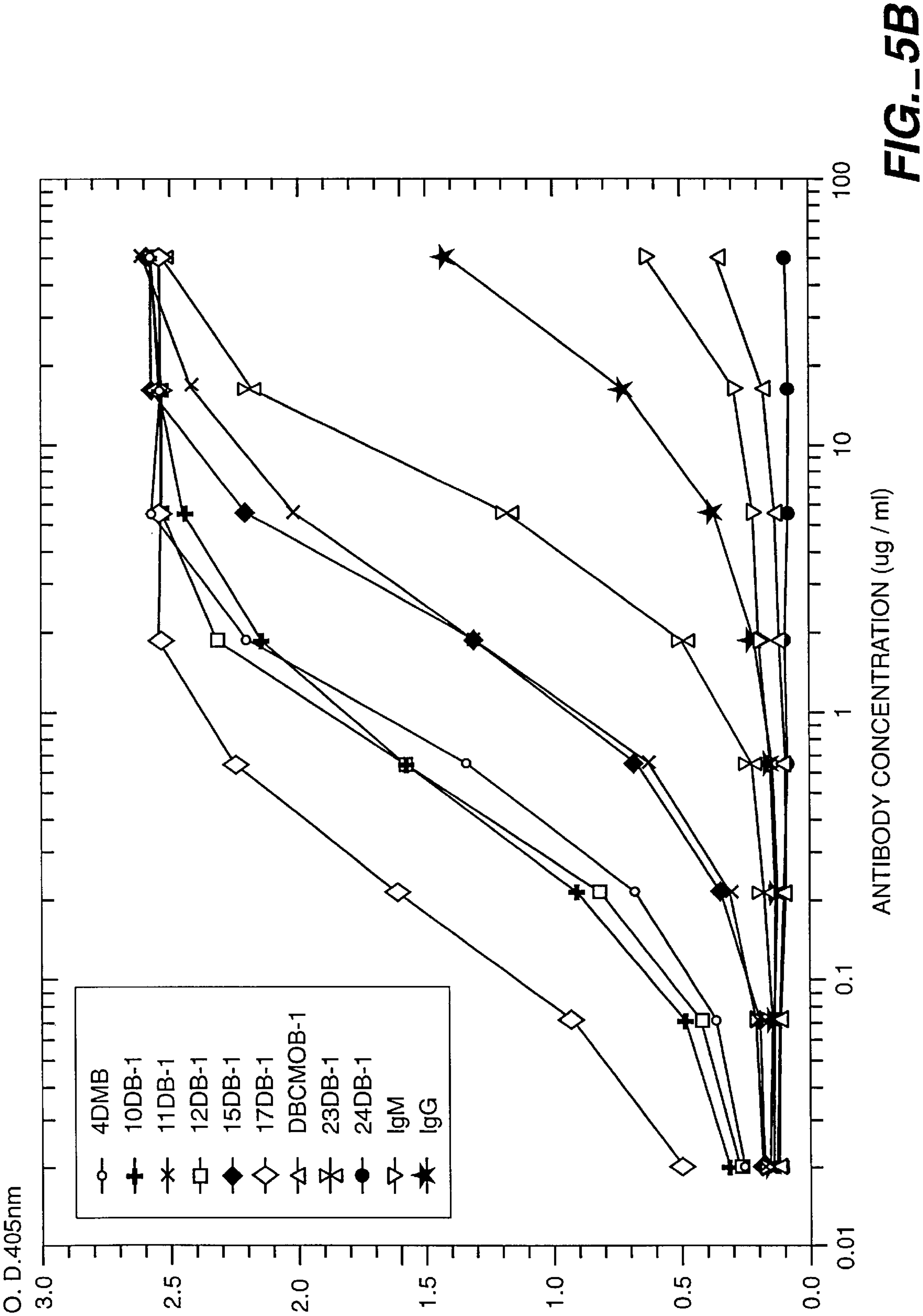
FIG._5B

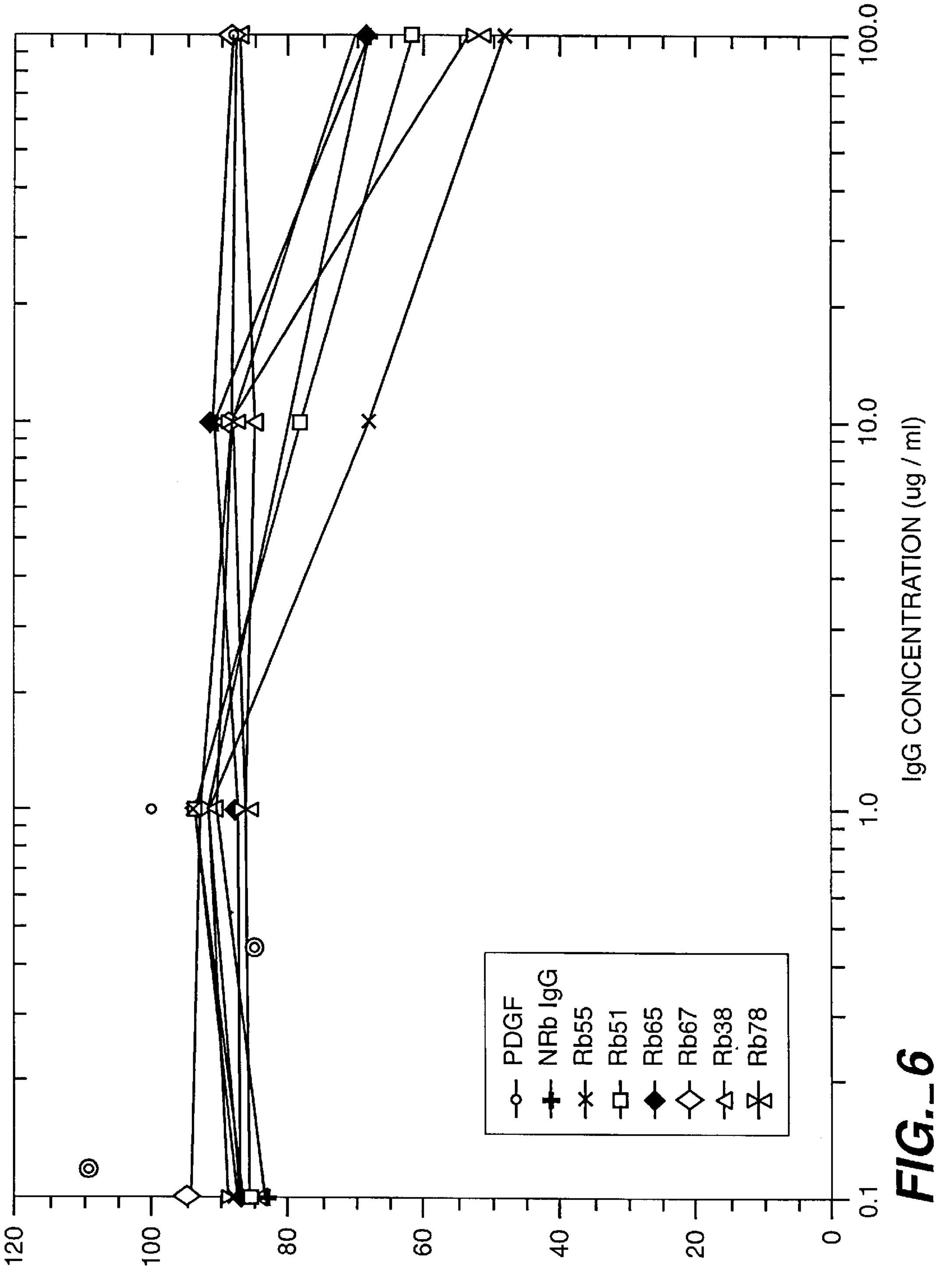
FIG._6

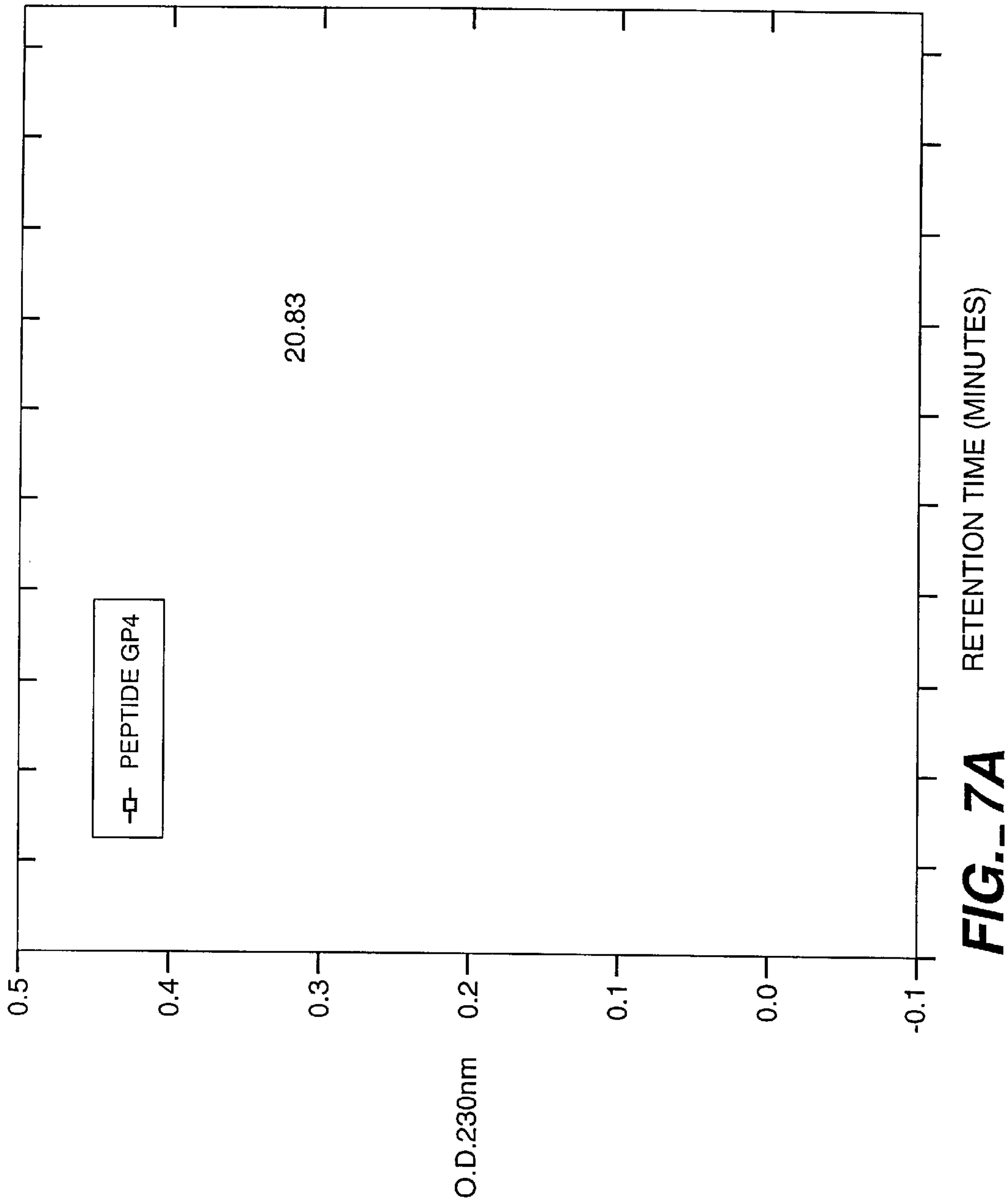
FIG._7A

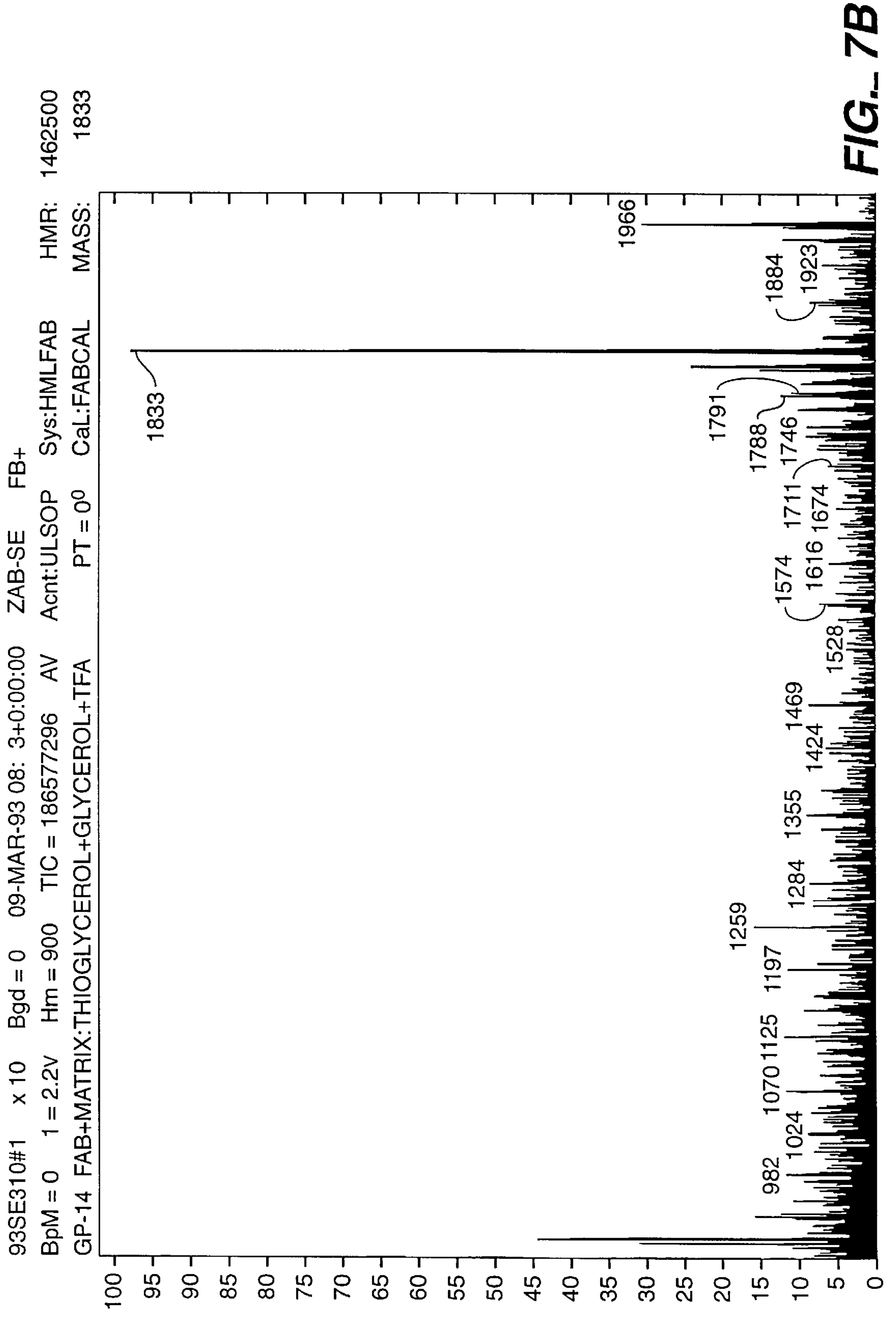
FIG._7B

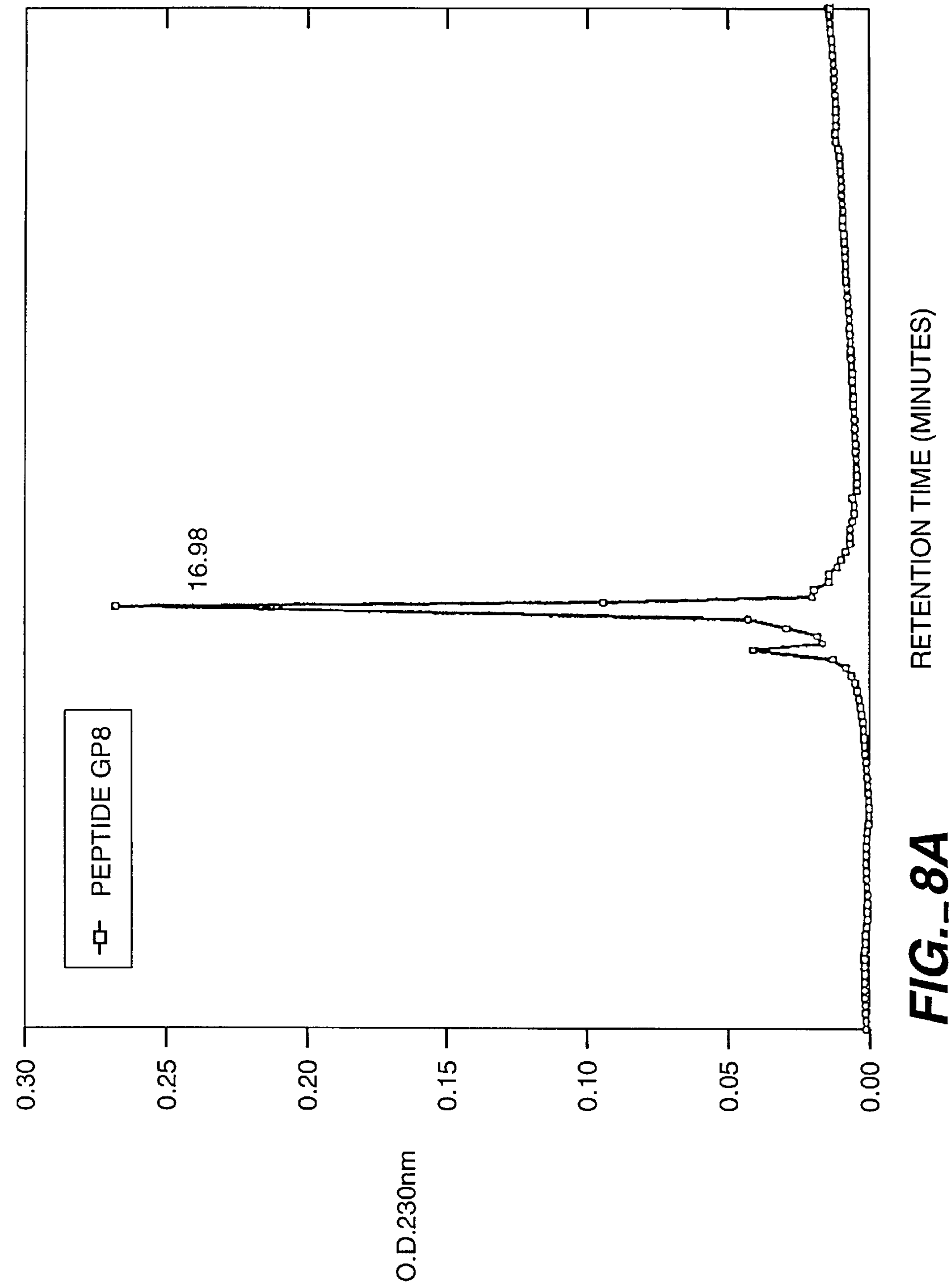
FIG._8A

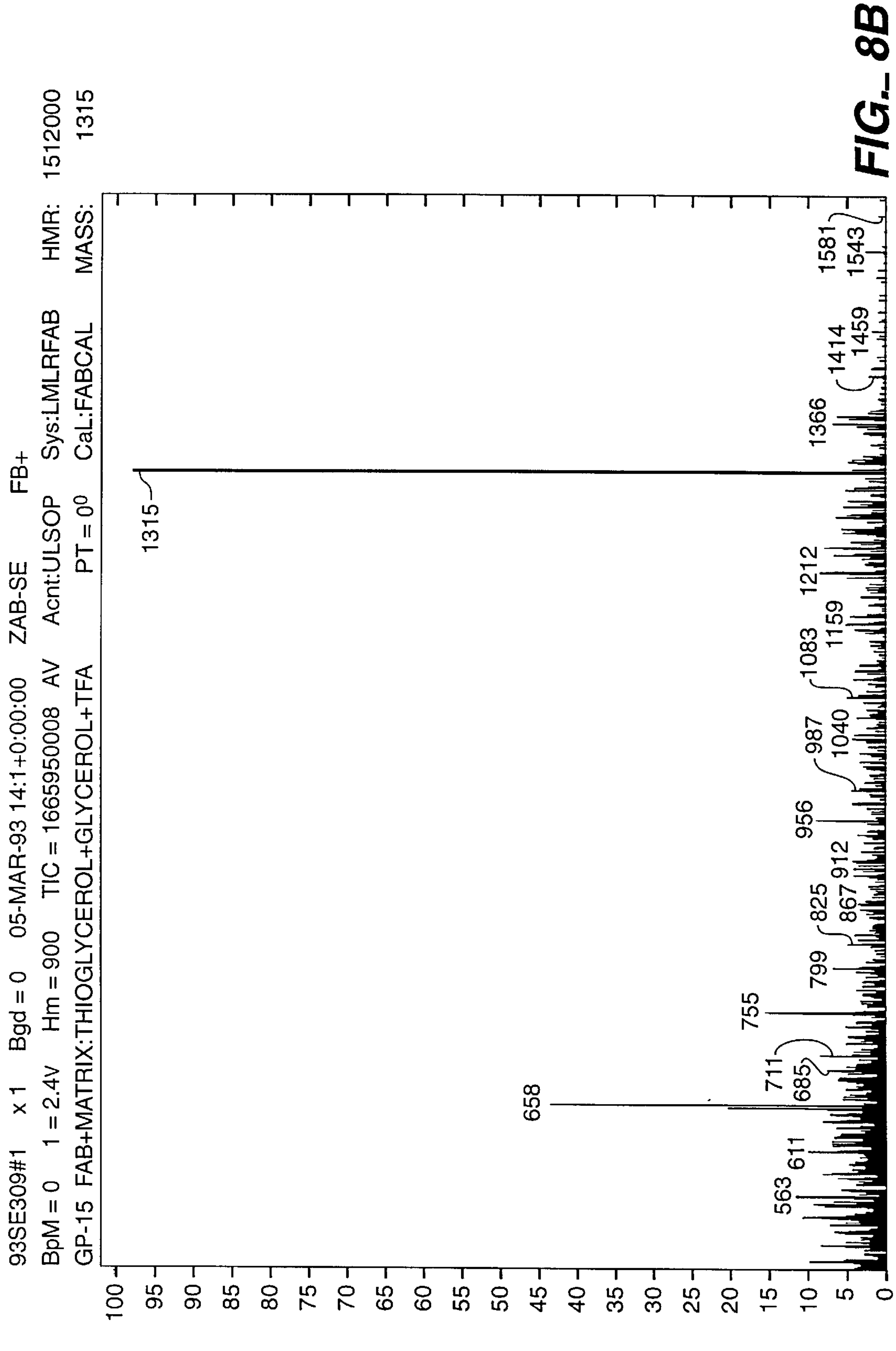
FIG._8B

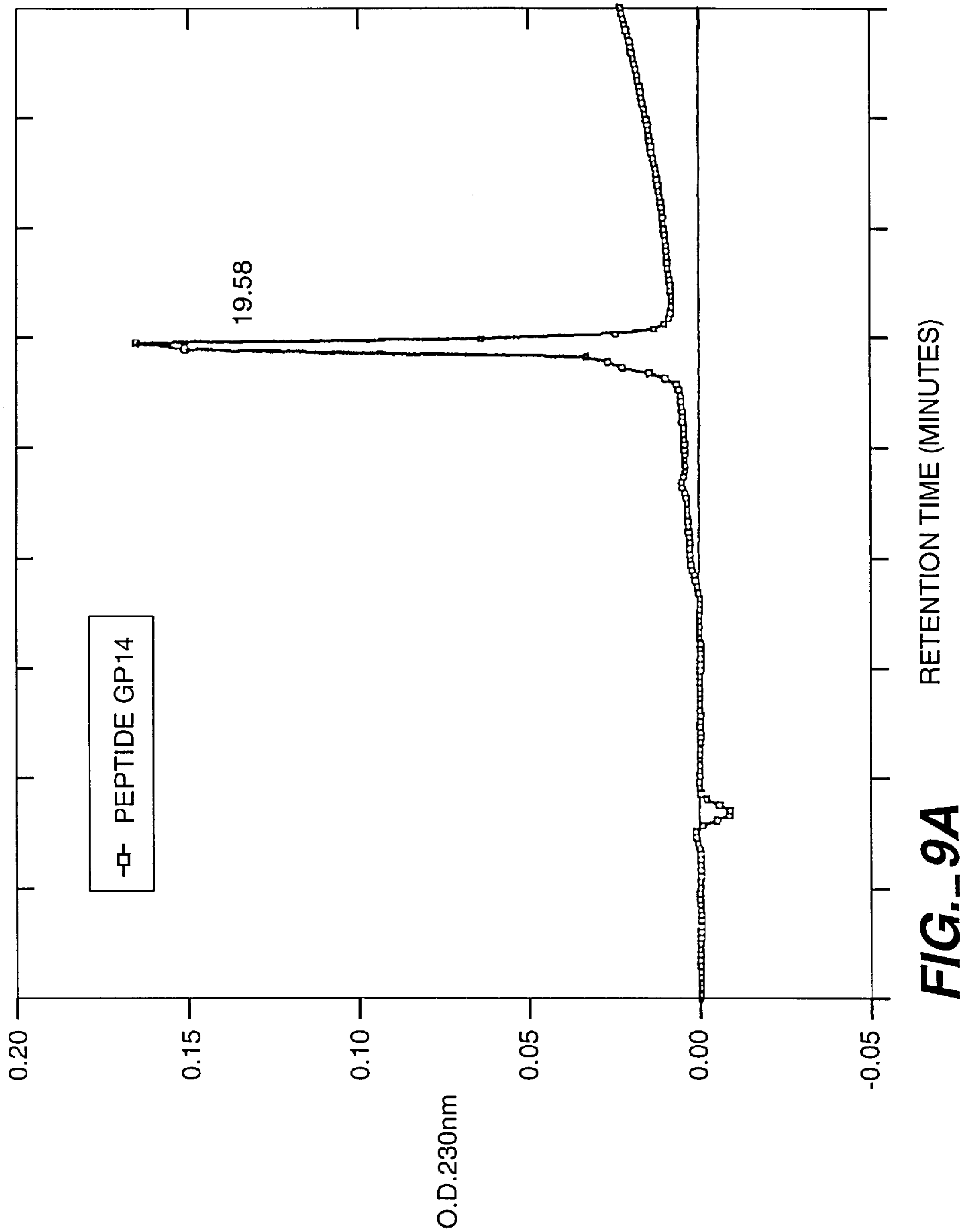
FIG._9A

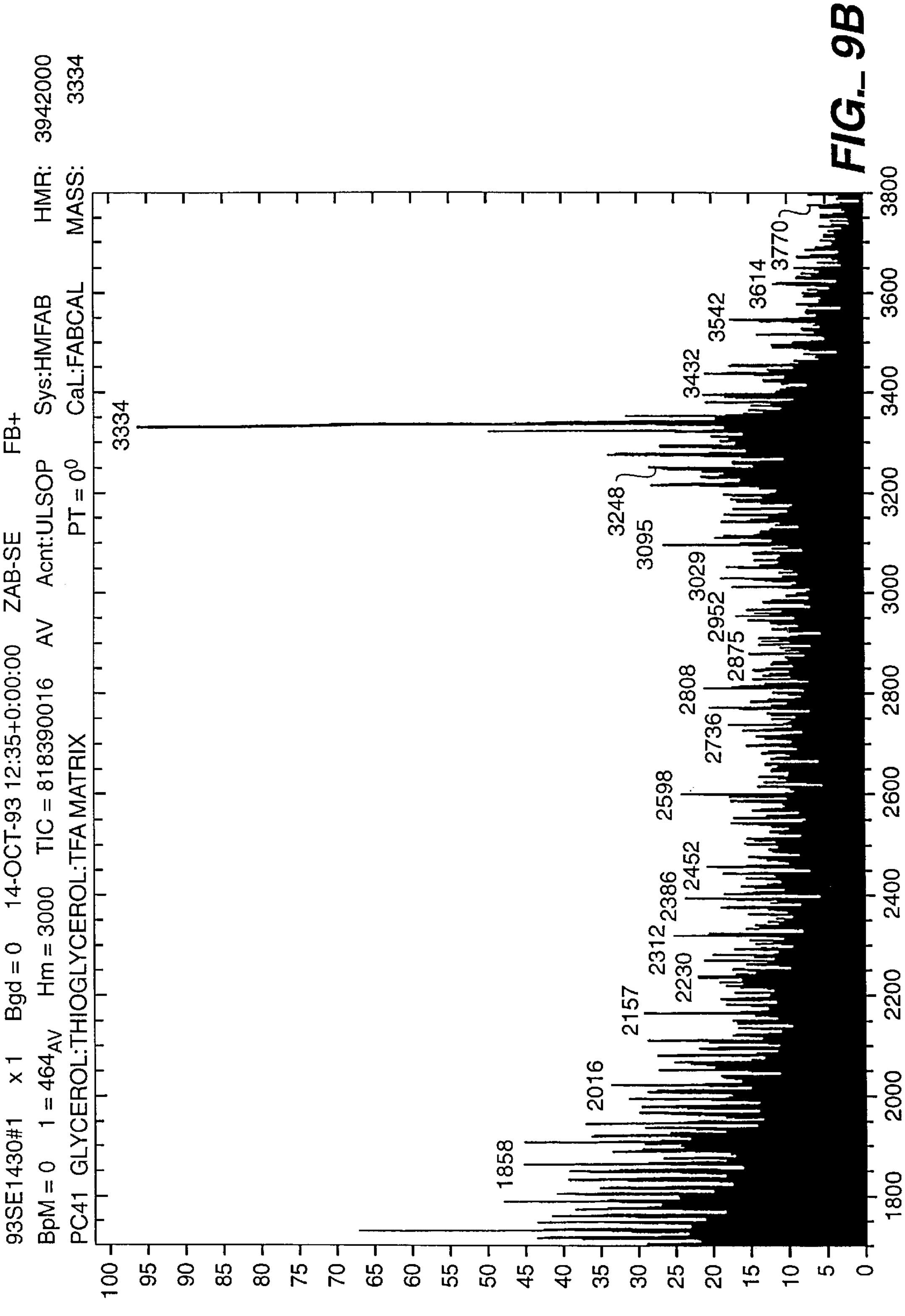
FIG._9B

PLATELET-DERIVED GROWTH FACTOR ANALOGUES

This is a division of application Ser. No. 08/635,007 filed Apr. 19, 1996 now U.S. Pat. No. 5,952,304 issued Sep. 14, 1999.

FIELD OF THE INVENTION

This invention relates to platelet-derived growth factor (PDGF) analogues and their use as cell antiproliferative agents.

DESCRIPTION OF THE RELATED ART

Relevant background material is incorporated herein by reference in the text to the listed references in the appended bibliography.

Platelet-derived growth factor (PDGF) is a potent mitogen for connective tissue cells and promotes the proliferation of fibroblasts and smooth muscle cells (SMC) [333]. The growth factor is a 28–31 KD dimeric, highly basic (Pi=9.8–10) glycoprotein consisting of two highly homologous (up to 60% sequence homology) polypeptide chains which are the products of distinct genes. The gene products designated A (on chromosome 7) and B (on chromosome 22) are assembled to form either a disulphide-linked heterodimer (PDGF-AB) or a homodimer (PDGF-AA or PDGF-BB). Analysis of the PDGF present in human platelets reveals that it is a mixture of all three dimeric forms with AB being the predominant form (up to 70%) [10;12]. The human prot-oncogene, c-sis, which codes for the PDGF-B chain [21] has been identified as the human homologue of the v-sis oncogene of the transforming retrovirus, simian sarcoma virus. This oncogene codes for the protein p28 v-sis which has been identified as PDGF-BB [5].

The cloning and amino acid sequencing of the A and B chains of human PDGF have shown that both chains are synthesised as precursor molecules with hydrophobic leader sequences and both chains undergo proteolytic cleavage at the N-termini during maturation. The B chain is also processed at the C-terminal end [21;20].

The three isoforms of PDGF exert their biological effects by binding with different affinities to two different receptor types, denoted α and β. Ligand binding induces dimerization of receptors; the A-subunit of PDGF binds to a-receptors whereas the B-subunit binds to both α- and β-receptors [2].

When PDGF diner is treated with reducing agents, the protein loses its biological activity irreversibly, suggesting that the protein conformation is disturbed by reduction of critical disulphide bonds [16]. PDGF has 8 cysteine residues which are highly conserved between the two chains. Six residues are involved in 3 intra-molecular disulphide bonds: Cys-16—Cys-60, Cys-49—Cys-97 and Cys-53—Cys-99. The other two cysteine residues are involved in asymmetrical inter-molecular disulphide bonds, Cys-43—Cys-52 [11].

A systematic analysis of the abilities of different peptides, derived from the PDGF-B chain sequence, to compete with $^{125}$I-PDGF-BB for binding to PDGF β-receptors, has led to the identification of two regions in the B-chain corresponding to amino acid residues 35–40 and 78–83 that seem important for receptor binding. A peptide corresponding to the two sequences (ANFLVW—EIVRKKP) (SEQ ID NOS: 12 and 13, respectively) has been found to be effective as an antagonist for PDGF, although detailed analysis has shown the pure peptide to be less active [6].

Site-directed mutagenesis studies, using deletion and substitution mutants of PDGF-BB or of the homologous v-sis gene as well as PDGF-A/B chimeras, have also identified a number of amino acid residues which are important for the biological activity of PDGF. The region Ile-25—Phe-38 has been identified as a binding domain by site directed mutagenesis of the v-sis gene [9]. Amino acid residue Asn-34 has been found to be essential for the PDGF-B-like transforming efficiency of PDGF-A/B chimera [27]. Using a different functional assay, which selects for mutants with reduced binding to both receptor types, Ile-30 and, to a lesser extent, Arg-27 have been shown to be important [3]. Basic polypeptides such as polypeptides such as polylysin and protamine sulphate inhibit PDGF binding to its receptor, suggesting a role for ligand positive charge in the binding interaction. A receptor binding domain has been assigned to a region at the C-terminal end which is rich with basic amino acid, residues Lys-80—Cys-97 [39]. This region contains the sequence Val-78—Arg-79—Lys-80—Lys-81—Pro-82, (SEQ ID NO:14) which is conserved in both the A and B chains, and therefore may be involved in the binding of both chains to PDGF α-receptor. A mutant PDGF-A chain in which the cationic sequence Arg-Lys-Lys has been replaced by the sequence Glu-Glu-Glu displays a marked reduction in both binding affinity for PDGF α-receptor and mitogenic activity in fibroblast cells [7]. Initial studies with neutralizing monoclonal antibodies raised to PDGF-BB indicates that the segment between Thr-20 and Cys-43 represents a surface domain of PDGF-BB and contains amino acid residues involved in receptor binding [22].

Recently, the crystal structure of the homodimeric BB isoform of human recombinant PDGF has been determined [26]. The protein polypeptide chain is folded into two highly twisted anti-parallel pairs of β-strands and contains an unusual knotted arrangement of three intramolecular disulphide bonds. Dimerization leads to the clustering of three surface loops at each end of the elongated dimer, which most probably form the receptor recognition sites. The three loops are: loop I: Ile-25—Leu -38, loop II: Cys-53—Val-58 and loop III: Val-78— Lys-81.

Antibodies to PDGF would be extremely useful in the study of PDGF processing and biosynthesis. It has been difficult to make high avidity antibodies against PDGF, maybe because the molecule is conserved between species and only recently have monoclonal antibodies against PDGF, become available [22;34;12;38]. Rabbit and goat antisera to PDGF have been made to the two chains using protein purified from human platelets or recombinant protein or synthetic peptides, some showing chain specificity and neutralizing activity [28;17;13;37;30]. None of the antibodies raised to peptides however have been capable of recognising the native molecule or able to neutralize its biological activities.

PDGF has been implicated in many biological systems. Originally, the close similarity between PDGF and the transforming factor involved in SSV transformation led to the concept that over-production of the factor was involved in the development of human malignancies [14]. Examination of many tumour cell lines shows that the A and B chains are commonly expressed in such cell lines [15;24]. In general, aberrant expression of PDGF or of PDGF receptors is likely to be involved in the stimulation of the growth of certain tumours. In addition, over-activity of PDGF could also be part of the development of certain non-malignant disorders involving an excess of cell proliferation. Examples include atherosclerosis, where PDGF-induced stimulation of smooth muscle cell proliferation could contribute to the thickening of the intima of affected vessels [32], as well as chronic fibrotic processes, where PDGF could be involved in the stimulation of connective tissue cell proliferation. Ferns et al [8] showed that in a rat experimental model of angioplasty, polyclonal antibodies to PDGF administered intravenously inhibited smooth muscle cell accumulation in the intima of injured arteries, while administration of PDGF induced SMC proliferation in the media by 2–3 fold and, more significantly, increased SMC migration from the media to the intima by 20-fold [19].

However, PDGF does have a normal function. PDGF and PDGF receptors are expressed in embryonic tissues and in the placenta [23;18] which suggests a function for PDGF during development. A role for PDGF in neuronal development has also been proven [25] and PDGF and its receptors are present in the peripheral and central nervous systems [40;36]. PDGF is known to stimulate growth as well as chemotaxis of connective tissue cells and also chemotaxis of inflammatory cells, which suggests a role in wound healing [4;35]. Recently, PDGF has been used in a clinical trial to look at its wound healing capability. Locally applied PDGF stimulates the healing of large bed sores [31]. PDGF β-receptors occur on capillary endothelial cells [29] and PDGF has weak angiogenic activity [29] which may suggest that its stimulatory effect is important in wound healing.

BRIEF SUMMARY OF THE INVENTION

The varied roles of PDGF, both beneficial and adverse, make PDGF agonists and antagonists highly desirable. They can be used as a replacement for PDGF in wound healing or as inhibitors of the adverse effects of PDGF. Antibodies with neutralizing activity, whether to the mitogenic effect of PDGF and/or the chemotactic effect can also be useful as inhibitors of PDGF adverse effects.

Accordingly, in one aspect the present invention provides novel PDGF peptide analogues and compositions consisting of or containing them for use as antiproliferative agents, particularly antiatherosclerotic, antiatherogenetic, anti-inflammatory or antifibrotic agents. The invention also provides such novel PDGF peptide analogues and compositions consisting of or containing them for use as PDGF agonists for use in wound healing.

Particular PDGF analogues according to the present invention are identified in Table 1 hereinbelow (SEQ ID NOS:1–7). Preferably, the PDGF peptide analogues of the invention, as prepared and used in other aspects and embodiments of the invention, are greater than about 90% pure, more preferably greater than about 95% pure, even more preferably greater than about 99% pure.

Pharmaceutical compositions in accordance with the present invention preferably comprise one or more of the PDGF analogues of the invention together with a pharmaceutically acceptable diluent and/or carrier. Suitable carriers/diluents are well known in the art and include saline or other sterile aqueous media, optionally including additional components such as buffer salts and preservatives, or sugars, starches, salts or mixtures thereof.

Peptides according to the present invention may be provided for use in any suitable form appropriate to the protocol of administration and/or the needs of a patient.

Apart from the pharmaceutically acceptable compositions referred to above, the peptides may for example be provided, either singly or in combination, in lyophilized or freeze dried solid forms.

Within the scope of the invention are linked peptides comprising a first analogue selected from the group consisting of GP1, (SEQ ID NO:1) GP2, (SEQ ID NO:1) GP3, (SEQ ID NO:2) GP4, (SEQ ID NO:2) GP9 (SEQ ID NO:3) and GP10 (SEQ ID NO:3) (as identified in Table 1 hereinbelow) and a second peptide analogue selected from the group consisting of GP5, (SEQ ID NO:4) GP6, (SEQ ID NO:4) GP7, (SEQ ID NO:5) GP8, (SEQ ID NO:5) GP21a, (SEQ ID NO:6) GP21 (SEQ ID NO:7) and GP22 (SEQ ID NO:7) (as identified in Table 1 hereinbelow), The invention further provides the novel PDGF peptide analogues for use in assays and kits for assays.

It is to be understood that within the scope of the present invention are peptide analogues as described and identified herein in which one or more amino acids are substituted with other amino acids, or in which there is inserted a spacer, for example a dithiol group or a diamino group or multiples of amino acid residues, e.g. glycine, as shown in Table 2 hereinbelow, peptides GP11, (SEQ ID NO:8) GP12, (SEQ ID NO:8) GP13 (SEQ ID NO:9) and GP14 (SEQ ID NO:9). The spacer may also be a homo- or hetero-bifunctional crosslinker, for example the heterobifunctional crosslinker N-(4-carboxy-cyclohexyl-methyl)-maleimide, as shown in Table 3 hereinbelow, peptides GP20 and GP23, (SEQ ID NO:10 and 11, respectively) providing generally of course that the essential activity of the peptide remains substantially unchanged.

The invention further provides the synthesis and use of cyclic peptides such as those derived from GP4 (SEQ ID NO:2) and GPB 8 (SEQ ID NO:5) as shown in Table 4 below, peptides GP24 (SEQ ID NO:1) and GP25 (SEQ ID NO:6).

The invention further provides the novel PDGF peptide analogues for use in assays and kits for assays, either in the free form or linked to a carrier molecule such as a protein or a solid particle, as well as modified peptides with e.g. biotin or fluorescein isothiocyanate, such as those shown in Table 5 hereinbelow, peptides GP15, GP16, GP19, GP17 and GP18.

In a second aspect, the present invention provides a method of inhibiting or stimulating cell proliferation, particularly smooth muscle cell, 3T3-fibroblast cell, connective tissue cell or inflammatory cell proliferation, by use or administration, particularly to a host, of an effective amount of a PDGF peptide analogue as defined above.

The invention further provides a method of inhibiting or stimulating PDGF-induced DNA synthesis comprising use or administration, such as to a host, of an effective amount of a PDGF peptide analogue as defined above.

In a further aspect, the present invention provides PDGF peptide analogues as defined above for use in inhibiting or stimulating growth and/or chemotaxis of cells such as those identified above.

In yet a further aspect, the present invention provides the above-defined PDGF peptide analogues, particularly the linked peptide analogues of the invention, for use as immunogens for the production of polyclonal and monoclonal antibodies to PDGF, especially for diagnostic, prognostic and therapeutic uses. Such methods of production of polyclonal and monoclonal antibodies are also within the scope of the invention.

In yet another aspect of the present invention, the novel PDGF analogues are provided for and used in methods of inhibiting PDGF-induced DNA synthesis, for example by use of or administration of an effective amount of one or more of the above defined PDGF peptide analogues.

Administration of peptides of the invention in any of the methods described herein may be via any suitable protocol. Preferably, administration to a host, especially a human host, is by intravenous injection or infusion, and may be systemic or topical. Such administration of peptides of the invention is in such an amount as to give the desired effective result of the peptide's activity at the intended site. Thus, a quantity which constitutes an "effective" amount may depend upon various parameters, such as body weight of the patient, degree of activity required, intended site of activity, severity of the condition to be treated or prevented, all of which will be well understood and appreciated by persons skilled in the art.

Generally, an amount (or total amount) of peptide will be administered which gives a concentration in plasma of from about 1 to about 100 mg $ml^{-1}$, more preferably from about 1 to about 10 mg $ml^{-1}$.

BRIEF DESCRIPTION OF THE DRAWINGS

The present invention will now be described in further detail, with reference to the accompanying drawings, in which:

FIG. 1 shows relative mitogenic effects of various PDGF related peptides;

FIGS. 2A and 2B show the results of a $^{125}$I-PDGF binding assay, as described further below;

FIGS. 3A and 3B show the results of titrations of, respectively, anti-Tg-GP4 vs.GP4 and anti-Tg-GP8 vs.GP8;

FIGS. 4A and 4B show the results of titrations of, respectively, anti-Tg-GP4 vs.PDGF-BB and anti-Tg-GP4 vs.FGF and EGF;

FIGS. 5A and 5B show the results of titrations of selected poly- and monoclonal antibodies by direct ELISA against PDGF-BB;

FIG. 6 shows the inhibition of radiolabelled PDGF-BB binding to human smooth muscle cells by anti-peptide antibodies; and FIGS. 7A and 7B, 8A and 8B, and 9A and 9B show the HPLC and mass spectroscopy profiles of peptides GP4, GP8 and GP14, respectively.

DETAILED DESCRIPTION OF THE INVENTION

METHODS

1) Synthesis of PDGF-BB Peptide Analogues

A series of PDGF-BB related peptides were synthesised, with or without modifications, by solid-phase on a Milligen 9050 Pepsynthesizer, using the FMOC-polyamide continuous method, as listed in Table 1 hereinbelow.

Acetylation of the N-terminal end of the peptides was performed after the completion of the synthesis. The resin was acetylated on the solid-support with 45% acetic anhydride in dimethylformamide. Deprotection and cleavage of the resin were carried out in the normal manner.

Biotinylation and FITC labelling were carried out while the peptides were still attached to the resin and prior to deprotection. Biotin-caproate-N-hydroxysucccinimide (B-NHS) and fluorescein isothiocaynate were used to label the free N-terminal end of the peptides.

All peptides were purified to at least 95% homogeneity by HPLC and their molecular weights determined by mass spectroscopy. FIGS. 7, 8 and 9 show examples of the HPLC and ma ss spectroscopy profiles of peptides GP4, GP8 and GP14, respectively.

2) Effect of PDGF Peptides on Fibroblast Cells in Culture

The stimulatory or inhibitory effect of the peptides on the murine fibroblast cell line Swiss 3T3.A31 were investigated using the [$^3$H]-thymidine uptake assay as described by Raines & Ross [28].

3) Effect of PDGF Peptides on $^{125}$I-PDGF-BB Binding to 3T3 Cells and Human Smooth Muscle Cells p PDGF-BB binding inhibition assay was performed as described by Engstrom et al [6]. A murine fibroblast cell line 3T3.A31 and human aortic smooth muscle cells were used.

4) Production of Antisera to PDGP-Peptides

Rabbits and mice were immunised with the peptides either in the free form mixed with Freund's adjuvant or conjugated to a carrier protein (Thyroglobulin or keyhole haemocyanin). Antisera were tested for antibody production to the peptides and PDGF using ELISA, dot blot assays and SDS-PAGE followed by Western blotting.

5) Effect of Anti-PDGF Peptides Antibodies on $^{125}$I-PDGF Binding to Human Smooth Muscle cells The IgGs of the polyclonal anti-PDGF peptides antisera were purified from the antisera by affinity chromatography on a protein G-Sepharose column as described by the manufacturers (Pharmacia, Uppsala, Sweden). The effect of the IgG on the binding of radiolabelled PDGF-BB to human smooth muscle cells was investigated using essentially the same procedure as for the peptides (method 3 above). In the test, peptides were replaced with IgG.

Results

The peptides were tested for their ability to stimulate thymidine uptake in the cells in culture.

FIG. 1 shows an example of the results obtained with some of the peptides. Peptide GP4 showed the highest stimulatory effect acting as an agonist for PDGF-BB. The mitogenic effect of GP4 was almost completely abolished upon reduction and alkylation of the C-terminal end cysteine residue. This strongly suggests that the peptide is acting via the formation of a dimeric form during the incubation with the cells and that it is the dimerisation which produces the increase in the stimulatory activity. This conclusion is also supported by the low stimulatory effect of peptide GP2 which has the same amino acid sequence as GP4 but without the C-terminal cysteine.

Peptide GP8 was not as stimulatory as GP4.

Some of the peptides were tested for their ability to inhibit the binding of radiolabelled PDGF-BB to 3T3 cells. Both GP4 and GP8 showed modest inhibition of binding at the concentrations tested, as illustrated in FIG. 2A. Peptides GP20 and GP14 were potent inhibitors of labelled PDGF binding to human smooth muscle cells, as shown in FIG. 2B.

Rabbits immunised with GP4 and GP8 peptides linked to thyroglobulin produced high titre antibodies to the corresponding immunising peptide as determine by ELISA, as illustrated in FIGS. 3A and 3B.

One of the rabbits immunised with GP4 also produced antibodies reactive with native PDGF-BB, and had no cross reactivity with human recombinant fibroblast growth factor (FGF) and epidermal growth factor (EGF). This is illustrated in FIG. 4.

Tables 6, 7 and 8 hereinbelow summarise the results of immunochemical characterisation of polyclonal and monoclonal antisera raised to PDGF-derived peptides.

Western immunoblot analysis of polyclonal antisera reactivity with native and reduced PDGF-BB (Table 6) shows that peptides GP4 and GP21a produced antibodies that reacted with the native PDGF. The competitive ELISA data are shown in Table 7. 15 monoclonal antibody hybridomas raised to peptide GP4 coupled to thyroglobulin were immunochemically characterised as shown in Table 8. FIGS. 5A and 5B show typical titration curves for polyclonal and monoclonal antisera against PDGF-BB.

The IgG fraction from rabbits immunised with peptides GP4 and GP21a were effective in inhibiting the binding of radio-labelled PDGF-BB to human smooth muscle cells in culture, as shown in FIG. 6.

TABLE 1

| PDGF-B CHAIN PEPTIDES | |
|---|---|
| LOOP I | |
| $^{25}$I-S-R-R-L-I-D-R-T-N-A-N-F-L$^{38}$ | GP1 |
| Ac-$^{25}$I-S-R-R-L-I-D-R-T-N-A-N-F-L$^{38}$ | GP2 |
| $^{25}$I-S-R-R-L-I-D-R-T-N-A-N-F-L$^{38}$-C | GP3 |
| Ac-$^{25}$I-S-R-R-L-I-D-R-T-N-A-N-F-L$^{38}$-C | GP4 |
| $^{25}$I-S-R-R-L-I-D-R-T-N-A-N-F-L-V-W-P-P-C$^{43}$ | GP9 |

TABLE 1-continued

| PDGF-B CHAIN PEPTIDES | |
|---|---|
| Ac-$^{25}$I-S-R-R-L-I-D-R-T-N-A-N-F-L-V-W-P-P-C$^{43}$ | GP10 |
| LOOP III | |
| $^{73}$R-K-I-E-I-V-R-K-K$^{81}$ | GP5 |
| AC-$^{73}$R-K-I-E-I-V-R-K-K$^{81}$ | GP6 |
| $^{73}$R-K-I-E-I-V-R-K-K$^{81}$-C | GP7 |
| AC-$^{73}$R-K-I-E-I-V-R-K-K$^{81}$-C | GP8 |
| $^{73}$R-K-I-E-I-V-R-K-K-P-I-F-K-K-A-T-V$^{89}$ | GP21a |
| $^{73}$R-K-I-E-I-V-R-K-K-P-I-F-K-K-A-T-V$^{89}$-C | GP21 |
| AC-$^{73}$R-K-I-E-I-V-R-K-K-P-I-F-K-K-A-T-V$^{89}$-C | GP22 |

TABLE 2

| PDGF-B CHAIN PEPTIDES (LOOP I & LOOP III using Glvevl spacers) | |
|---|---|
| $^{25}$I-S-R-R-L-I-D-R-T-N-A-N-F-L$^{38}$-(G-G-G-G)-$^{73}$R-K-I-E-V-R-K-K$^{81}$-C | GP11 |
| Ac-$^{25}$I-S-R-R-L-I-D-R-T-N-A-N-F-L$^{38}$-(G-G-G-G)-$^{73}$R-K-I-E-I-V-R-K-K$^{81}$-C | GP12 |
| $^{25}$I-S-R-R-L-I-D-R-T-N-A-N-F-L$^{38}$-(G-G-G-G-G-G)-$^{73}$R-K-I-E-I-V-R-K-K$^{81}$-C | GP13 |
| Ac-$^{25}$I-S-R-R-L-I-D-R-T-N-A-N-F-L$^{38}$-(G-G-G-G-G-G)-$^{73}$R-K-I-E-I-V-R-K-K$^{81}$-C | GP14 |

TABLE 3

| CROSS-LINKED PDGF LOOP I & LOOP III PEPTIDES | |
|---|---|
| Ac-$^{25}$I-S-R-R-L-I-D-R-T-N-A-N-F-L-V-W-P-P-C$^{43}$-(SMCC)-$^{73}$R-K-I-E-I-V-R-K-K$^{81}$-C | GP20 |
| Ac-$^{25}$I-S-R-$R_z$-L-I-D-R-T-N-A-N-L$^{38}$-C-(SMCC)-$^{73}$R-K-I-E-I-V-R-K-K$^{81}$-C | GP23 |

{SMCC:-N-(4-carboxy-cyclohexyl-methyl)-maleimide OR any heterobifunctional cross-linker}

TABLE 4

CYCLIC PDGF-B CHAIN PEPTIDES

LOOP I

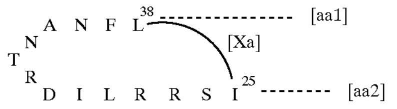

GP24

LOOP III

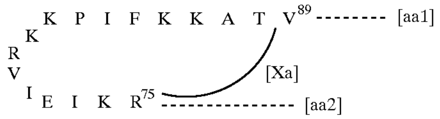

GP25

(Xa = bridging spacer arm)
aa1 = amino acid/acids of C-terminus
aa2 = amino acid/acids of N-terminus

TABLE 5

| AFFINITY-LABELLED PDGF-B CHAIN PEPTIDES | |
|---|---|
| LOOP I | |
| X-$^{25}$I-S-R-R-L-I-D-R-T-N-A-N-F-L$^{38}$ | GP15 |
| X-$^{25}$I-S-R-R-L-I-D-R-T-N-A-N-F-L$^{38}$-C | GP16 |
| X-$^{25}$I-S-R-R-L-I-D-R-T-N-A-N F-L-V-W-P-P-C$^{43}$ | GP19 |
| LOOP III | |
| X-$^{73}$R-K-I-E-I-V-R-K-K$^{81}$ | GP17 |
| X-$^{73}$R-K-I-E-I-V-R-K-K$^{81}$-C | GP18 |

(X = Biotin or FITC)

TABLE 6

Polyclonal anti-PDGF peptides antisera analysis by western Blot.

| Antibody | Immunogen | vs PDGF Ser-1/100 | vs PDGF Ser-1/1000 | vs PDGF Ser-1/10000 | vs RED-PDGF Ser-1/100 | vs RED-PDGF Ser-1/10000 |
|---|---|---|---|---|---|---|
| Rb 86 | GP4 | – | – | – | ++ | – |
| Rb 65 | Tg-GP4 | ++++ | +++ | – | +++++ | +++++ |
| Rb 66 | Tg-GP4 | +++ | +++ | – | +++++ | +++ |
| Rb 109 | GP10 | – | – | – | ++ | – |
| Rb 37 | GP10 | – | – | – | +++ | ++ |
| Rb 38 | Tg-GP10 | – | – | – | ++++ | +++ |
| Rb 39 | Tg-GP10 | – | – | – | +++++ | ++++ |
| Rb 112 | Tg-GP10 | – | – | – | +++ | + |
| Rb 67 | Tg-GP8 | – | – | – | ++++ | ++ |

TABLE 6-continued

Polyclonal anti-PDGF peptides antisera analysis by western Blot.

| Antibody | Immunogen | vs PDGF Ser-1/100 | vs PDGF Ser-1/1000 | vs PDGF Ser-1/10000 | vs RED-PDGF Ser-1/100 | vs RED-PDGF Ser-1/10000 |
|---|---|---|---|---|---|---|
| Rb 68 | Tg-GP8 | + | – | – | ++ | – |
| Rb 78 | GP21a | +++++ | +++++ | + | +++++ | +++++ |
| Rb 91 | GP21a | – | – | – | +++ (1/200) | + (1/20,000) |
| Rb 113 | Tg-GP4 | – (1/200) | – | – | – (1/200) | – (1/20,000) |
| Rb 114 | Tg-GP4 | ++ (1/200) | – | – | ++++ (1/200) | + (1/20,000) |

+++++ Very strong
++++ Strong
+++ Medium
++ Weak
+ Very weak
– Negative

TABLE 7

Competitive ELISA analysis of polyclonal anti-PDGF-BB peptides antisera

| Antibody | Immunogen | titer | GP4 IC50 | GP10 IC50 | GP21a IC50 | GP8 IC50 | PDGF IC50 |
|---|---|---|---|---|---|---|---|
| Rb 86 | GP4 | | | | | | |
| Rb 65 | Tg-GP4 | 1/243,000 | 3 nM | 3 nM | NONE | >6000 nM | 180 nM |
| Rb 66 | Tg-GP4 | 1/27,000 | <2 nM | <2 nM | NONE | NONE | NONE |
| Rb 109 | GP10 | 1/10,000 | 2 nM | 4 nM | NONE | NONE | NONE |
| Rb 37 | GP10 | 1/27,000 | 20 nM | 10 nM | NONE | NONE | NONE |
| Rb 38 | Tg-GP10 | 1/27,000 | 150 nM | 74 nM | NONE | NONE | NONE |
| Rb 39 | Tg-GP10 | 1/100,000 | 2 nM | 2 nM | NONE | NONE | NONE |
| Rb 112 | Tg-GP10 | 1/243,000 | 2 nM | 3 nM | NONE | NONE | NONE |
| Rb 67 | Tg-GP8 | 1/243,000 | Not Sig | Not Sig | Not Sig | 2 nM | 200 nM |
| Rb 68 | Tg-GP8 | 1/243,000 | Not Sig | Not Sig | Not Sig | <2 nM | 30 nM |
| Rb 78 | GP21a | 1/15,000 | NONE | NONE | 100 nM | NONE | NONE |
| Rb 91 | GP21a | ND | ND | ND | ND | ND | ND |
| Rb 113 | Tg-GP4 | 1/100,000 | | | | | |
| Rb 114 | Tg-GP4 | 1/2,000 | | | | | |

Peptides tried up to 6000 nM, PDGF up to 200 nM

TABLE 8

Reactivities of monoclonal antibodies to peptide GP4
sub-class, ELISA, CELIA and Western blot analysis

| ANTIBODY | Sub-class | ELISA TITER | ELISA PDGF* | BLOT RED PDGF | BLOT PDGF | CELIA GP4 | CELIA GP10 | CELIA GP21a | CELIA GP8 | CELIA PDGF** |
|---|---|---|---|---|---|---|---|---|---|---|
| 1 DMB | IgG1 | ND | –ve | + | – | – | – | – | – | – |
| 2 DMB | IgG1 | ND | –ve | + | – | 2 uM | 2 uM | – | – | – |
| 3 DMB | IgG1 | ND | –ve | + | – | – | – | – | – | – |
| 4 DMB | IgG1 | ND | –ve | +++ | – | 150 nM | 150 nM | – | – | – |
| 9 DB-1 | IgG1 | 1/10 | –ve | – | – | 1 uM | 1.2 uM | – | – | +10%? |
| 10 DB-1 | IgG1 | 1/243 | 10% | +++++ | – | 400 nM | >6 uM | – | – | +10%? |
| 11 DB-1 | IgM | 1/2 | 30% | ++ | – | – | – | – | – | +175%? |
| 12 DB-1 | IgG1 | 1/243 | –ve | +++++ | – | 2 uM | – | – | – | – |
| 13 DB-1 | IgG1 | 1/10 | –ve | – | – | 200 nM | 400 nM | – | – | – |
| 15 DB-1 | IgM | 1/9 | 31% | ++ | – | – | – | – | – | +356%? |
| 17 DB-1 | IgG1 | 1/81 | 30% | +++++ | – | 180 nM | 3 uM | – | – | +25%? |
| 19 DB-1 | IgG1 | 1/1000 | –ve | – | – | 18 nM | 18 nM | – | – | +10%? |
| 21 DB-1 | IgG1 | 1/1000 | –ve | – | – | 18 NM | 30 nM | – | – | – |
| 22 DB-1 | IgG1 | 1/1000 | –ve | – | – | 20 nM | 25 nM | – | – | – |

*Expressed as a percentage of OD given by 500 ng/ml Rb anti-PDGF (Bachem)
**An increase in signal may be caused by cross-linking
In CELIAS, peptides tried up to 6000 nM, PDGF up to 200 nM

REFERENCES

1 Bar, R. S. et al (1989) *Endocrinology,* 1841–1848.
2. Claesson-Welsh, L. (1993) *Cytokines,* 5, 31–43.
3. Clements, X. et al (1991) *EMBO J.,* 10, 4113–4120.
4. Deuel, T. F., Senior, R. M., Huang, J. S. & Griffin, G. L. (1981) *J. Clin. Invest.,* 69, 1046–1049.
5. Doolittle, R. F., Hunkapiller, M. W., Hood, L. E. & 4 others (1983) *Science,* 221, 275–277.
6. Engstrom, U., Engstrom, A., Ernlund, A., Westermark, B. & Heldin, C-H. (1992) *J. Biol. Chem.,* 267, 16581–16587.
7. Fenstermaker, R. A. et al (1993) *J. Biol. Chem.,* 268, 10482–10489.
8. Ferns, G. A. A. et al (1991) *Science,* 253, 1129–1132.
9. Giese, N. A., LaRochelle, W. J., May-Siroff, M., Robbins, K. C. & Aaronson, S. A. (1990) *Mol. Cell Biol.,* 10, 5496–5501.
10. Hamacher, A., Hellman, U., Johnsson, A., Osttman, A., Gunnarsson, K., Westermark, B., Wasteson, A. & Heldin, C-H. (1988) *J. Biol. Chem.,* 263, 16493–16498.
11. Haniu, M., Rohde, M. F. & Kenney, W. C. (1993) *Biochemistry* 32, 2431–2437.
12. Hart, C. E., Bailey, M., Curtis, D. A., Osborn, S., Raines, E., Ross, R. & Forstorm, J. W. (1990) *Biochemistry,* 29, 166–172.
13. Huang, J. S., Huang, S. S. & Deuel, T. F. (1983) *J. Cell Biol.,* 97, 383–388.
14. Heldin, C-H. (1992) *EMBO J.,* 11, 4251–4259.
15. Heldin, C-H. & Westermark, B. (1989) *British Med. Bull.,* 45, 453–464.
16. Heldin, C-H., Westermark, A., & Wasteson, A. (1981) *Exp. Cell Res.,* 136, 255–261.
17. Heldin, C-H., Westermark, A. & Wasteson, A. (1981) *Proc. Natl. Acad, Sci.,* 78, 3664–3668.
18. Holmrgren, L., Claesson-Welsh, L., Heldin, C-H. & Ohlsson, R. (1992) *Growth Factors,* 6, 219–232.
19. Jawein, A. et al (1992) *J. Clin. Invest.,* 89, 507–511.
20. Johnsson, A., Betsholtz, C., Heldin, C. H. & Westermark, B. (1986) *EMBO J.,* 5, 1535–1541.
21. Joseph, S. F., Guo, C., Ratner, L. & Wong-Staal, F. (1984) *Science,* 223, 487–490.
22. LaRochelle, W., Robbins, K. C. & Aaranson, S. A. (1989) *Mol. Cell. Biol.,* 9, 3538–3542.
23. Mercola, M. et al (1990) *Dev. Biol.,* 138, 114–122.
24. Nister, M. et al (1988) *Cancer Res.,* 48, 3910–3918.
25. Noble, M. et al (1988) *Nature,* 333, 560–562.
26. Oefner, C. et al (1992) *EMBO J.,* 11, 3921–3926.
27 Ostman, A., Andersson, M., Hellman, U. & Heldin, C-H. (1991) *J. Biol. Chem,* 266, 10073–10077.
28. Raines, E. W. & Ross, R. (1982) *J. Biol. Chem.,* 257, 5154–5160.
29. Risau, W. (1992) *Growth Factors,* In Press.
30. Robins, K. C. et al (1983) *Nature,* 305, 605–609.
31. Robson, M. C. et al (1992) *Lancet,* 339, 23–25.
32. Ross, R. (1993) *Nature,* 362, 801–809.
33. Ross, R., Raines, E. W. & Bowen-Pope, D. F. (1986) *Cell,* 46, 155–169.
34. Shiraishi, T. et al (1989) *Clin. Chim. Acta,* 184, 65–74.
35 Siegbhan, A., Hammacher, A., Westermark, B. & Heldin, C-H. (1990) *J. Clin. Invest.,* 85, 916–920.
36. Smits, A. et al (1991) *Proc. Natl, Acad. Sci.,* 88, 8159–8163.
37 Thyberg, J. et al (1990) *J. Cell Sci.,* 97, 219–229.
38. Vassbotn, F. S., Langeland, N., Hagen, I. & Holmsen, A. (1990) *Biochem. Biophys. Acta,* 1054, 246–249.
39. Vogel, S. & Hoppe, J. (1989) *Biochemistry,* 28, 2961–2966.
40. Yeh, H. J. et al (1991) *Cell,* 64, 209–216.

What is claimed is:

1. A platelet-derived growth factor peptide analogue consisting essentially of:

(i) a first sequence selected from the group consisting of:

| | |
|---|---|
| $^{25}$I-S-R-R-L-I-D-R-T-N-A-N-F-L$^{38}$ | (GP1) (SEQ ID NO:1) |
| Ac-$^{25}$I-S-R-R-L-I-D-R-T-N-A-N-F-L$^{38}$ | (GP2) (SEQ ID NO:1) |
| $^{25}$I-S-R-R-L-I-D-R-T-N-A-N-F-L$^{38}$-C | (GP3) (SEQ ID NO:2) |
| Ac-$^{25}$I-S-R-R-L-I-D-R-T-N-A-N-F-L$^{38}$-C | (GP4) (SEQ ID NO:2) |
| $^{25}$I-S-R-R-L-I-D-R-T-N-A-N-F-L-V-W-P-P-C$^{43}$ | (GP9) (SEQ ID NO:3) |
| and | |
| Ac-$^{25}$I-S-R-R-L-I-D-R-T-N-A-N-F-L-V-W-P-P-C$^{43}$ | (GP10) (SEQ ID NO:3); |

(ii) a second sequence linked to the first sequence and selected from the group consisting of:

| | |
|---|---|
| $^{73}$R-K-I-E-I-V-R-K-K$^{81}$ | (GP5) (SEQ ID NO:4) |
| Ac-$^{73}$R-K-I-E-I-V-R-K-K$^{81}$ | (GP6) (SEQ ID NO:4) |
| $^{73}$R-K-I-E-I-V-R-K-K$^{81}$-C | (GP7) (SEQ ID NO:5) |
| Ac-$^{73}$R-K-I-E-I-V-R-K-K$^{81}$-C | (GP8) (SEQ ID NO:5) |
| $^{73}$R-K-I-E-I-V-R-K-K-P-I-F-K-K-A-T-V$^{89}$ | (GP21a) (SEQ ID NO:6) |
| $^{73}$R-K-I-E-I-V-R-K-K-P-I-F-K-K-A-T-V$^{89}$-C | (GP21) (SEQ ID NO:7) |
| and | |
| Ac-$^{73}$R-K-I-E-I-V-R-K-K-P-I-F-K-K-A-T-V$^{89}$-C | (GP22) (SEQ ID NO:7). |

2. A peptide selected from the group consisting of:

| | |
|---|---|
| $^{25}$I-S-R-R-L-I-D-R-T-N-A-N-F-L$^{38}$-(G-G-G-G)-$^{73}$R-K-I-E-I-V-R-K-K$^{81}$-C | (GP11) (SEQ ID NO:8) |
| Ac-$^{25}$I-S-R-R-L-I-D-R-T-N-A-N-F-L$^{38}$-(G-G-G-G)-$^{73}$R-K-I-E-I-V-R-K-K$^{81}$-C | (GP12) (SEQ ID NO:8) |
| $^{25}$I-S-R-R-L-I-D-R-T-N-A-N-F-L$^{38}$-(G-G-G-G-G-G)-$^{73}$R-K-I-E-I-V-R-K-K$^{81}$-C | (GP13) (SEQ ID NO:9) |
| Ac-$^{25}$I-S-R-R-L-I-D-R-T-N-A-N-F-L$^{38}$-(G-G-G-G-G-G)-$^{73}$R-K-I-E-I-V-R-K-K$^{81}$-C | (GP14) (SEQ ID NO:9) |
| Ac-$^{25}$I-S-R-R-L-I-D-R-T-N-A-N-F-L-V-W-P-P-C$^{43}$-(SMCC)-$^{73}$R-K-I-E-I-V-R-K-K$^{81}$-C | (GP20) (SEQ ID NO:10) |
| and | |
| AC-$^{25}$I-S-R-R-L-I-D-R-T-N-A-N-F-L$^{38}$-C-(SMCC)-$^{73}$R-K-I-E-I-V-R-K-K$^{81}$-C | (GP23) (SEQ ID NO:11) |

wherein SMCC is N-(4-carboxy-cyclohexyl-methyl)-maleimide.

3. A platelet-derived growth factor peptide analogue comprising the following sequence:

| | |
|---|---|
| Ac-$^{25}$I-S-R-R-L-I-D-R-T-N-A-N-F-L$^{38}$-(G-G-G-G-G-G)-$^{73}$R-K-I-E-I-V-R-K-K$^{81}$-C. | (GP14) (SEQ ID NO:9) |

4. A platelet-derived growth factor peptide analogue consisting essentially of:

(i) a first sequence selected from the group consisting of:

| | |
|---|---|
| $^{25}$I-S-R-R-L-I-D-R-T-N-A-N-F-L$^{38}$ | (GP1) (SEQ ID NO:1) |
| Ac-$^{25}$I-S-R-R-L-I-D-R-T-N-A-N-F-L$^{38}$ | (GP2) (SEQ ID NO:1) |
| $^{25}$I-S-R-R-L-I-D-R-T-N-A-N-F-L$^{38}$-C | (GP3) (SEQ ID NO:2) |
| Ac-$^{25}$I-S-R-R-L-I-D-R-T-N-A-N-F-L$^{38}$-C | (GP4) (SEQ ID NO:2) |
| $^{25}$I-S-R-R-L-I-D-R-T-N-A-N-F-L-V-W-P-P-C$^{43}$ | (GP9) (SEQ ID NO:3) |
| and | |
| Ac-$^{25}$I-S-R-R-L-I-D-R-T-N-A-N-F-L-V-W-P-P-C$^{43}$ | (GP10) (SEQ ID NO:3); |

(ii) a second sequence linded to the first sequence and selected form the group consisting of:

| | |
|---|---|
| $^{73}$R-K-I-E-I-V-R-K-K$^{81}$ | (GP5) (SEQ ID NO:4) |
| Ac-$^{73}$R-K-I-E-I-V-R-K-K$^{81}$ | (GP6) (SEQ ID NO:4) |
| $^{73}$R-K-I-E-I-V-R-K-K$^{81}$-C | (GP7) (SEQ ID NO:5) |
| Ac-$^{73}$R-K-I-E-I-V-R-K-K$^{81}$-C | (GP8) (SEQ ID NO:5) |
| $^{73}$R-K-I-E-I-V-R-K-K-P-I-F-K-K-A-T-V$^{89}$ | (GP21a) (SEQ ID NO:6) |
| $^{73}$R-K-I-E-I-V-R-K-K-P-I-F-K-K-A-T-V$^{89}$-C | (GP21) (SEQ ID NO:7) |
| and | |
| Ac-$^{73}$R-K-I-E-I-V-R-K-K-P-I-F-K-K-A-T-V$^{89}$-C | (GP22) (SEQ ID NO:7); and |

(iii) a spacer located between said first and second sequences and selected from the group consisting of multiples of amino acid residues and heterobifunctional crosslingers.

5. The peptide of claim 4 wherein said spacer is polyglycyl.

6. The peptide of claim 4 wherein said spacer is -(G-G-G-G-G-G)-.

7. The peptide of claim 4 wherein said spacer is SMCC.

8. The peptide of claim 4 wherein said first sequence is GP1 (SEQ ID NO:1) or GP2 (SEQ ID NO:1).

9. The peptide of claim 4 wherein said second sequence is GP7 (SEQ ID NO:5).

10. The peptide of claim 4 wherein said first sequence is GP2 (SEQ ID NO:1) and said second sequence is GP7 (SEQ ID NO:5).

11. The peptide of claim 10 wherein said spacer is polyglycyl.

12. A pharmaceutical composition comprising one or more peptides according to any of claim 1, claim 2, claim 3, and claim 4, together with a pharmaceutically acceptable diluent and/or carrier.

13. A pharmaceutical composition according to claim 12, wherein the peptide(s) is present in an amount such as to give a concentration thereof in plasma of a host to which the composition is administered of from 1 to 100 mg $ml^{-1}$.

* * * * *

```
                    SEQUENCE LISTING


(1) GENERAL INFORMATION:

   (iii) NUMBER OF SEQUENCES: 14


(2) INFORMATION FOR SEQ ID NO:1:

    (i) SEQUENCE CHARACTERISTICS:
         (A) LENGTH: 14 amino acids
         (B) TYPE: amino acid
         (C) STRANDEDNESS: single
         (D) TOPOLOGY: both

   (ii) MOLECULE TYPE: peptide

   (ix) FEATURE:
         (A) NAME/KEY: Modified-site
         (B) LOCATION: 1
         (D) OTHER INFORMATION: /note= "Ile may be acetylated"

   (ix) FEATURE:
         (A) NAME/KEY: Cross-links
         (B) LOCATION: 1
         (D) OTHER INFORMATION: /note= "A cyclic peptide may be formed
              by linking Ile 1 with Leu 14 via bridging spacer arm"

   (ix) FEATURE:
         (A) NAME/KEY: Binding-site
         (B) LOCATION: 1
```

-continued (D) OTHER INFORMATION: /note= "Ile may be bound to biotin or FITC"

(xi) SEQUENCE DESCRIPTION: SEQ ID NO:1:

```
Ile Ser Arg Arg Leu Ile Asp Arg Thr Asn Ala Asn Phe Leu
1               5                   10
```

(2) INFORMATION FOR SEQ ID NO:2:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Ile may be acetylated"

(ix) FEATURE:
(A) NAME/KEY: Binding-site
(B) LOCATION: 1
(D) OTHER INFORMATION: /note= "Ile may be bound to biotin or FITC"

(xi) SEQUENCE DESCRIPTION: SEQ ID NO:2:

```
Ile Ser Arg Arg Leu Ile Asp Arg Thr Asn Ala Asn Phe Leu
1               5                   10

Cys
15
```

(2) INFORMATION FOR SEQ ID NO:3:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Ile may be acetylated"

(ix) FEATURE:
(A) NAME/KEY: Binding-site
(B) LOCATION: 1
(D) OTHER INFORMATION: /note= "Ile may be bound to biotin or FITC"

(xi) SEQUENCE DESCRIPTION: SEQ ID NO:3:

```
Ile Ser Arg Arg Leu Ile Asp Arg Thr Asn Ala Asn Phe Leu
1               5                   10

Val Trp Pro Pro Cys
15
```

(2) INFORMATION FOR SEQ ID NO:4:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide -continued (ix) FEATURE:
(A) NAME/KEY: Modified-site
(B) LOCATION: 1
(D) OTHER INFORMATION: /note= "Arg may be acetylated"

(ix) FEATURE:
(A) NAME/KEY: Binding-site
(B) LOCATION: 1
(D) OTHER INFORMATION: /note= "Arg may be bound to biotin or FITC"

(xi) SEQUENCE DESCRIPTION: SEQ ID NO:4:

```
Arg Lys Ile Glu Ile Val Arg Lys Lys
1               5
```

(2) INFORMATION FOR SEQ ID NO:5:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Arg may be acetylated"

(ix) FEATURE:
(A) NAME/KEY: Binding-site
(B) LOCATION: 1
(D) OTHER INFORMATION: /note= "Arg may be bound to biotin or FITC"

(xi) SEQUENCE DESCRIPTION: SEQ ID NO:5:

```
Arg Lys Ile Glu Ile Val Arg Lys Lys Cys
1               5                   10
```

(2) INFORMATION FOR SEQ ID NO:6:

(i) SEQUENCE CHARACTERISTICS:
(A) LENGTH: 17 amino acids
(B) TYPE: amino acid
(C) STRANDEDNESS: single
(D) TOPOLOGY: both (ii) MOLECULE TYPE: peptide (ix) FEATURE:
(A) NAME/KEY: Cross-links
(B) LOCATION: 1
(D) OTHER INFORMATION: /note= "A cyclic peptide may be formed by linking Arg 1 with Val 17 via a bridging spacer arm"

(xi) SEQUENCE DESCRIPTION: SEQ ID NO:6:

```
Arg Lys Ile Glu Ile Val Arg Lys Lys Pro Ile Phe Lys Lys
1               5                   10

Ala Thr Val
15
```

(2) INFORMATION FOR SEQ ID NO:7:

(i) SEQUENCE CHARACTERISTICS:
(A) LENGTH: 18 amino acids
(B) TYPE: amino acid
(C) STRANDEDNESS: single
(D) TOPOLOGY: linear (ii) MOLECULE TYPE: peptide -continued (ix) FEATURE:
(A) NAME/KEY: Modified-site
(B) LOCATION: 1
(D) OTHER INFORMATION: /note= "Arg may be acetylated"

(xi) SEQUENCE DESCRIPTION: SEQ ID NO:7:

Arg Lys Ile Glu Ile Val Arg Lys Lys Pro Ile Phe Lys Lys
1 5 10

Ala Thr Val Cys
15

(2) INFORMATION FOR SEQ ID NO:8:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Ile may be acetylated"

(xi) SEQUENCE DESCRIPTION: SEQ ID NO:8:

Ile Ser Arg Arg Leu Ile Asp Arg Thr Asn Ala Asn Phe Leu
1 5 10

Gly Gly Gly Gly Arg Lys Ile Glu Ile Val Arg Lys Lys Cys
15 20 25

(2) INFORMATION FOR SEQ ID NO:9:

(i) SEQUENCE CHARACTERISTICS:
(A) LENGTH: 30 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Ile may be acetylated"

(xi) SEQUENCE DESCRIPTION: SEQ ID NO:9:

Ile Ser Arg Arg Leu Ile Asp Arg Thr Asn Ala Asn Phe Leu
1 5 10

Gly Gly Gly Gly Gly Gly Arg Lys Ile Glu Ile Val Arg Lys
15 20 25

Lys Cys
30

(2) INFORMATION FOR SEQ ID NO:10:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide (ix) FEATURE:
(A) NAME/KEY: Cross-links
(B) LOCATION: 19..20

-continued

```
          (D) OTHER INFORMATION: /note= "Cross-linker may be
               N-(4-carboxy-cyclohexyl-methy
               other heterobifunctional cross-linker."

    (ix) FEATURE:
          (A) NAME/KEY: Modified-site
          (B) LOCATION: 1
          (D) OTHER INFORMATION: /note= "Ile may be acetylated"

    (xi) SEQUENCE DESCRIPTION: SEQ ID NO:10:

Ile Ser Arg Arg Leu Ile Asp Arg Thr Asn Ala Asn Phe Leu
1               5                   10

Val Trp Pro Pro Cys Arg Lys Ile Glu Ile Val Arg Lys Lys
15                  20                  25

Cys


(2) INFORMATION FOR SEQ ID NO:11:

     (i) SEQUENCE CHARACTERISTICS:
          (A) LENGTH: 25 amino acids
          (B) TYPE: amino acid
          (C) STRANDEDNESS: single
          (D) TOPOLOGY: linear

    (ii) MOLECULE TYPE: peptide

    (ix) FEATURE:
          (A) NAME/KEY: Cross-links
          (B) LOCATION: 15..16
          (D) OTHER INFORMATION: /note= "Cross-linker may be
               N-(4-carboxy-cyclohexyl-methy
               other heterobifunctional cross-linker."

    (ix) FEATURE:
          (A) NAME/KEY: Modified-site
          (B) LOCATION: 1
          (D) OTHER INFORMATION: /note= "Ile may be acetylated"

    (xi) SEQUENCE DESCRIPTION: SEQ ID NO:11:

Ile Ser Arg Arg Leu Ile Asp Arg Thr Asn Ala Asn Phe Leu
1               5                   10

Cys Arg Lys Ile Glu Ile Val Arg Lys Lys Cys
15                  20                  25


(2) INFORMATION FOR SEQ ID NO:12:

     (i) SEQUENCE CHARACTERISTICS:
          (A) LENGTH: 6 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:12:

Ala Asn Phe Leu Val Trp
1               5


(2) INFORMATION FOR SEQ ID NO: 13:

     (i) SEQUENCE CHARACTERISTICS:
          (A) LENGTH: 7 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:13:
```

-continued

```
Glu Ile Val Arg Lys Lys Pro
1               5

(2) INFORMATION FOR SEQ ID NO:14:

     (i) SEQUENCE CHARACTERISTICS:
          (A) LENGTH: 5 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:14:

Val Arg Lys Lys Pro
1               5
```